(12) United States Patent
Hagadorn

(10) Patent No.: US 7,858,817 B2
(45) Date of Patent: Dec. 28, 2010

(54) METALLOCENE-SUBSTITUTED PYRIDYL AMINES, THEIR METAL COMPLEXES, AND PROCESSES FOR PRODUCTION AND USE THEREOF

(75) Inventor: John R. Hagadorn, Houston, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 29 days.

(21) Appl. No.: 12/045,486

(22) Filed: Mar. 10, 2008

(65) Prior Publication Data
US 2009/0227747 A1 Sep. 10, 2009

(51) Int. Cl.
*C07F 17/02* (2006.01)

(52) U.S. Cl. .................. 556/144; 556/143; 556/140; 556/138; 564/4

(58) Field of Classification Search ............ 556/152, 556/153, 154, 136, 144, 143, 138
See application file for complete search history.

(56) References Cited

U.S. PATENT DOCUMENTS

| | | | | |
|---|---|---|---|---|
| 6,034,240 | A | * | 3/2000 | La Pointe .................. 546/24 |
| 6,953,764 | B2 | | 10/2005 | Frazier et al. |
| 7,045,583 | B2 | | 5/2006 | Kuchta et al. |
| 2006/0247483 | A1 | | 11/2006 | McConville et al. |
| 2008/0153997 | A1 | | 6/2008 | Casty et al. |
| 2009/0270622 | A1 | * | 10/2009 | Kesselgruber et al. ........ 546/4 |

FOREIGN PATENT DOCUMENTS

| | | |
|---|---|---|
| EP | 1 842 860 | 10/2007 |
| JP | 1-226894 A * | 9/1989 |
| JP | 2001-181292 A * | 7/2001 |
| WO | WO 00/59961 | 10/2000 |
| WO | WO 01/74910 | 10/2001 |
| WO | WO 02/38268 | 5/2002 |
| WO | WO 02/38628 | 5/2002 |
| WO | WO 03/040095 | 5/2003 |
| WO | WO 03/040201 | 5/2003 |
| WO | WO 03/040202 | 5/2003 |
| WO | WO 2004/024739 | 3/2004 |
| WO | WO 2007/067965 | 6/2007 |
| WO | WO 2007/113168 A1 * | 11/2007 |
| WO | WO 2007/130242 | 11/2007 |

OTHER PUBLICATIONS

Cui et al., Dalton Trans., 2004, 1743-1751.*
Mamane et al., J. Org. Chem., 2005, 70, 8220-8223.*
P.D. Hustad et al., Continuous Production of Ethylene-Based Diblock Copolymers Using Coordinative Chain Transfer Polymerization, Macromolecules, vol. 40, No. 20, Oct. 2, 2007, pp. 7061-7064.

(Continued)

*Primary Examiner*—Rip A. Lee
(74) *Attorney, Agent, or Firm*—Catherine L. Bell

(57) ABSTRACT

This invention relates to new transition metal complexes for use in olefin polymerization and oligomerization. The active complex is a pyridine amide having a metallocenyl substituent as part of the ligand structure. The invention also relates to novel precursors for the ligand systems of such complexes obtained from metallocenyl-substituted pyridine compounds through sequences involving addition-condensation or lithium-halogen exchange (with subsequent metathesis) reactions.

12 Claims, 6 Drawing Sheets

OTHER PUBLICATIONS

T.R. Boussie et al., "Nonconventional Catalysts for Isotactic Propene Polymerization in Solution Developed by Using High-Throughput-Screening Technologies", Angew. Chem. Int. Ed., 2006, 45, pp. 3278-3283.

R.D.J. Froese et al., "Mechanism of Activation of a Hafnium Pyridyl-Amide Olefin Polymerization Catalyst: Ligand Modification by Monomer", J. Am. Chem. Soc., 2007, 129, pp. 7831-7840.

G.J. Domski et al., "Polymerization of α-Olefins with Pyridylamidohafnium Catalysts: Living Behavior and Unexpedted Isoselectivity from a Cs-Symmetric Catalyst Precursor", Macromolecules, 2007, 40, pp. 3510-3513.

Press Release, "Dow and Symyx Announce Discovery of New Class of Polyolefin Catalyst", Mar. 31, 2003.

"Finding Catalysts Faster—Symyx-Dow collaboration yields new class of polyolefin catalysts", C&En, Apr. 7, 2003, p. 10.

TRBoussie et al., "A Fully Integrated High-Throughput Screening Methodology for the Discovery of New Polyolefin Catalysts: Discovery of a New Class of High Temperature Single-Site Group (IV) Copolymerization Catalysts", J. Am. Chem. Soc., 2003, 125, pp. 4306-4317.

Mamane et al., Convenient Access to New Chiral Ferroceno-(iso)quinolines, Journal of Organic Chemistry, 2005, vol. 70, No. 20, pp. 8220-8223.

Gibson et al., Ferrocene-Substituted Bis(imino)pyridine Iron and Cobalt Complexes: Toward Redox-Active Catalysts for the Polymerization of Ethylene, Organometallics, 2006, vol. 25, No. 8, pp. 1932-1939.

* cited by examiner

METALLOCENE-SUBSTITUTED PYRIDYL AMINES, THEIR METAL COMPLEXES, AND PROCESSES FOR PRODUCTION AND USE THEREOF

FIELD OF THE INVENTION

The invention relates to reactive metallocenyl intermediates for use especially but not exclusively in making pyridyl amine ligand precursors. The invention further relates transition metal complexes incorporating ligands derived from the precursors for use as catalysts in olefin polymerization and oligomerization processes. Specifically, this invention relates to reactive metallocenyl intermediates, pyridyl amine ligand precursors made using such intermediates, transition metal complexes incorporating ligands derived from such precursors and processes for making these; as well as olefin polymerization and oligomerization processes using such transition metal complexes as catalysts.

BACKGROUND OF THE INVENTION

The specification describes transition metal complexes. The metal of the complex is coordinated to an ancillary ligand that is bulky and stably bonded to the transition metal. The ligand is derived from a neutral ligand precursor. The ligand may be coordinated to the transition metal by covalent bond and/or electron donation coordination.

Suitable transition metal complexes such as metallocenes and pyridine amine complexes may be used in olefin oligomerization, involving the linking of a limited number of monomer units or in olefin polymerization wherein numerous monomer units are joined to form a polymer chain.

The transition metal complexes are generally activated to perform their polymerization or oligomerization function. Activation involves, according to current theory, transformation of the neutral complex into a cation after interaction with a so-called activator.

The invention is especially concerned with pyridyl amine transition metal complexes of the type described in WO 02/038628 A2. An example of the preparation of ligand precursors is set out on pages 75-79 of WO 02/038628. A dihalopyridine is reacted with n-butyllithium and then dimethylformamide to produce a 2-bromo-6-formyl pyridine. This product is reacted with naphthylboronic acid to form 2-formyl-6-naphthylpyridine. This in turn is reacted with 2,6-diisopropylaniline to form 6-naphthyl-2-(2,6-diisopropylphenylimine)pyridine. This is reacted to give the amine with a free hydrogen atom on the bridging nitrogen atom. Page 78 discloses different ligands options.

There still is need for adding synthetic routes to broaden the performance envelopes catalysts of transition metal complexes having pyridyl-based ligands capable of reacting with alkenes.

SUMMARY OF THE INVENTION

In a first aspect the invention provides novel metallocenyl compounds for serving as an intermediate starting material in the formation of a neutral ancillary ligand precursor. Accordingly the invention provides a compound of the general formula (I):

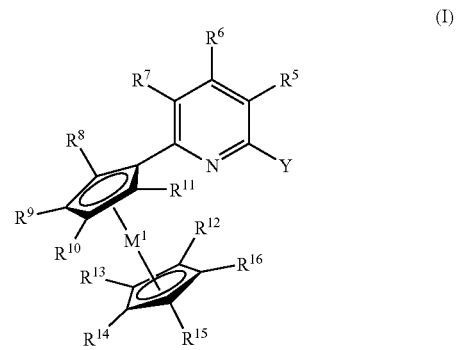

wherein $M^1$ is a metal atom selected from the group consisting of Fe, Ru, or Co; Y is a reactive moiety selected from the group consisting of —CHO, C(O)R$^4$ or a halogen, and $R^4$ to $R^{16}$ can be independently selected from the group consisting of hydrogen, alkyl, aryl, arylalkyl, halogen, alkoxy, aryloxy, amino, silyl, and two adjacent carbon atoms of at least one cyclopentadienyl moiety may be linked by a saturated or unsaturated cyclic moiety having from 3 to 6 carbon atoms, optionally containing a heteroatom. References to heteroatoms herein include nitrogen, silicon, phosphorus and oxygen.

The metal $M^1$ is preferably coordinated only to the two cyclopentadienyl groups. This limits the selection of $M^1$ to the metals indicated usually present in a stable 2 plus, $d^6$ state. The metallocenyl compound is preferably a ferrocenyl compound. By the term "reactive" is meant that the group may be used to couple the compound to other compounds in an addition-condensation reaction or a sequence involving a lithium-halogen exchange followed by a metathesis reaction. The term "cyclopentadienyl group" is used herein to include monocyclic but also polycyclic structures incorporating a cyclopentadienyl moiety and also additional saturated or aromatic cyclic moieties. Such enlarged structures further increase the bulk and modify the properties of the metallocenyl group and include multiple substituents that form a polycyclic fused ring system such as an indenyl or fluorenyl group. The 3 to 6 atoms do not include the carbon atoms of the cyclopentadienyl moiety itself.

The compounds may be synthesized starting from known compounds such as a metallocenyl boronic acid and a pyridine compound that can be coupled with the metallocenyl boronic acid. The compounds having a halogen group as a functional group can later be reacted for example to form silicon-containing moieties. The compound having an aldehyde or ketone as the functional group can later be reacted to provide a bridging group containing a carbon atom.

In a second aspect the invention provides a novel neutral ligand precursor that may be used in the synthesis of transition metal complexes. In this aspect the invention provides a compound having the general formula (II):

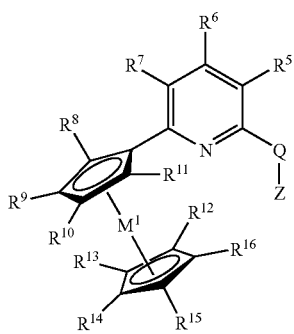

(II)

wherein $M^1$ is a metal atom selected from the group consisting of Fe, Ru, or Co; Q is —$CR^3R^4$— or —$SiR^3R^4$—; and $R^1$ to $R^{16}$ can be independently selected from the group consisting hydrogen, alkyl, aryl, arylalkyl, halogen, alkoxy, aryloxy, amino, silyl; Z is —$NR^1R^2$ or =$NR^2$ and two adjacent carbon atoms of at least one cyclopentadienyl moiety may be linked by a saturated or unsaturated cyclic moiety having from 3 to 6 carbon atoms, optionally containing a heteroatom and $R^1$ and $R^2$ in —$NR^1R^2$ and $R^3$ and $R^4$ in $CR^3R^4$— or —$SiR^3R^4$ may form a chain of from 3 to 6 carbon atoms, optionally including a heteroatom.

The functional group -Q-Z in the intermediate is linked to an amine with the bridging group Q being preferably in the form of a methylene, methine, or disubstituted silyl bridge to the nitrogen atom of the amine in moiety —Z.

In a third aspect of the invention there is provided a transition metal complex having the general formula (III):

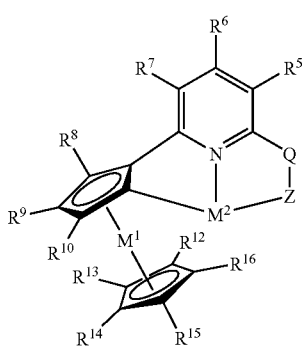

(III)

wherein $M^1$ is a metal atom selected from the group consisting of Fe, Ru, or Co; Q is —$CR^3R^4$— or —$SiR^3R^4$—; and $R^1$ to $R^{16}$ can be independently selected from the group consisting of hydrogen, alkyl, aryl, arylalkyl, halogen, alkoxy, aryloxy, amino, silyl and $M^2$ is a group 3, 4, 5, or 6 metal (IUPAC standard periodic table) with one to four additional donor and/or anionic ligands coordinated to $M^2$, Z is —$NR^1R^2$ or —$NR^2$ and two adjacent carbon atoms of at least one cyclopentadienyl moiety may be linked by a saturated or unsaturated cyclic moiety having from 3 to 6 carbon atoms, optionally containing a heteroatom and $R^1$ and $R^2$ in —$NR^1R^2$ and $R^3$ and $R^4$ in $CR^3R^4$— or —$SiR^3R^4$ may form a chain of from 3 to 6 carbon atoms, optionally including a heteroatom. In the formation of the complex, a carbon atom of one of the cyclopentadienyl groups bonds to $M^2$ and forms a cationic ligand.

The additional ligands for $M^2$ may be abstracted in the course of activation in the polymerization or oligomerization process. These additional anionic ligands can be independently selected from the group consisting of hydrogen, alkyl, aryl, arylalkyl, or halogen. The donor ligands may be a molecule containing a free electron pair such as tetrahydrofuran (thf) or a diethyl-ether.

In the complex $M^2$ may be a group 4 metal in which case suitably Z is —$NR^2$, or $M^2$ may be Cr in which case Z is advantageously —$NR^1R^2$.

The wide range of substitution options above may be further refined. $M^1$ may be Fe and $R^8$ to $R^{16}$ may be hydrogen. To the extent the carbon atoms and nitrogen atoms are substituted the alkyl, aryl, arylalkyl, silyl, aryloxy and alkoxy moieties may comprise from 1 to 20 carbon atoms and may be branched or linear. Where aryl, arylalkyl and aryloxy groups are concerned they contain at least 6 carbon atoms.

These complexes, in combination with appropriate activators, have activity as catalysts for olefin polymerization such as ethylene-based polymers or propylene-based polymers, including ethylene-octene polymerization. They may also have activity in ethylene oligomerization and may be highly active. Once the ligand precursors have been produced, the formation of the complexes is in accordance with techniques described generally in the literature such as WO 02/38628.

Accordingly, the invention also provides a catalyst system comprising the reaction product of a complex shown above and an activator selected from the group of alumoxane and non-coordinated anions.

In a fourth aspect of the invention, the complexes are used upon suitable activation, in linking olefinic monomers to form oligomers and polymers. According to this aspect the invention provides a polymerization process which comprises contacting an olefin monomer with a catalyst system, (e.g., a catalyst process and an activator) as disclosed above in which the transition metal $M^2$ is selected from a group 4 transition metal and especially hafnium or zirconium.

In a fifth aspect a synthesis sequence is provided which includes a process for producing a metallocenyl pyridine compound which comprises reacting a metallocenylboronic acid with a pyridyl compound containing at least one pyridyl-halogen or triflate group in the presence of a Pd catalyst, preferably 1,1'-bis(diphenylphosphino)ferrocene, and producing a compound of the general formula (I). This step may include coupling a di-halo-pyridine or a halo-pyridine-aldehyde or halo-pyridine-ketyl species with a metallocenyl-based boronic acid to produce an intermediate compound in which —Y is halogen or —CHO or —$C(O)R^4$. Further steps may include lithiating the compound in which —Y is halogen and reacting the lithio product with a mono- or dichloro silicon derivative and an amine or metal amido reagent, if necessary, or reacting the compound in which —Y is —CHO or —$C(O)R^4$ with an amine and subsequently with an organometallic reagent to form a ligand precursor the compound having the general formula (II). In a final step the amine derivative produced may be subjected to a protonolysis reaction between the ligand precursor and an organometallic reagent and then alkylation of the product by transmetalation, if necessary, or subjecting the imine derivative to an addition reaction of the imine ligand precursor with an organometallic reagent to produce a transition metal complex having the general formula (III).

For purposes of this invention and the claims thereto the following abbreviations are used: Ph is phenyl, Me is methyl, Bu is butyl, t-Bu is tertiary-butyl, Mes is mesityl, PrPh is propylphenyl, iPr is isopropyl, iPrPh is isopropylphenyl, Cy is cyclohexyl, Tol is toluoyl, tol is toluoyl, Dipp is diisopropylphenyl, Bn is benzyl, THF is tetrahydrofuran, thf is tetrahydrofuran, ppf is 1,1'-bis(diphenylphosphino)ferrocene. The chemical compositions of certain ligand abbreviations used (e.g., $L^{FcCH2NHDipp}$) are shown in Charts 1 and 2. These abbreviations are not intended to be accurate chemical formulas, but instead present some useful information in a convenient manner.

DETAILS OF THE INVENTION

Figure 1:
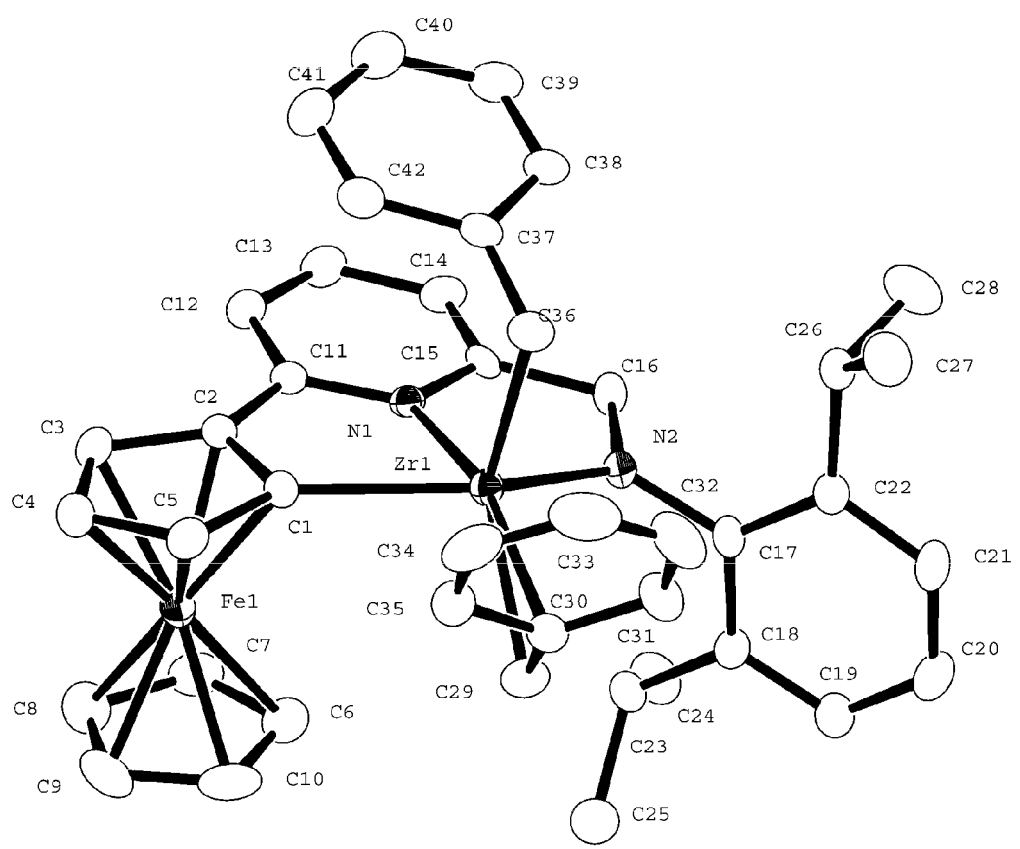
FIG. 1 is an illustration of the molecular structure of $[L^{FcCH2NHDipp}]ZrBn_2$ as determined by single-crystal X-ray diffraction.

The metallocene group can be introduced into the ligand framework using established Pd-catalyzed coupling methods described, for example, by Miyaura and Suzuki (Chem. Rev., 1995, 95, pages 2457-2483). Typically, this involves the reaction of a metallocenylboronic acid with a halo-substituted pyridine species. The presence of a Pd catalyst is highly desirable. Optimal results may be obtained using (dppf)PdCl$_2$, where dppf=1,1'-bis(diphenylphosphino)ferrocene. Other Pd catalysts, including Pd(PPh$_3$)$_4$ (Ph=phenyl) and (PEPPSI)PdCl$_2$ (PEPPSI=1,3-bis(2,6-diisopropylphenyl) imidazolidene) are also useful. The dppf catalyst is commercially available and can be purchased from Strem. The metallocenylboronic acids can be readily prepared from metallocenyllithium or metallocenylmagnesium reagents or by other methods. Early examples are given by Nesmeyanov and coworkers (Chem. Ber., 1960, 93, pages 2717-2729) and by Schechter and coworker (J. Org. Chem., 1961, 26, pages 1034-1037). Ferrocenylboronic acid is also commercially available. Our studies used ferrocenylboronic acid purchased from Sigma-Aldrich.

The metallocenylboronic acid intermediate may contain an Fe, Ru, or Co as the central metal ion. The cyclopentadienyl rings can be unsubstituted or substituted or can be fused rings such as indenyl or fluorenyl-based structures. Numerous examples of metallocenylboronic acids and esters are known (Scifinder, January 2008). The boronic esters are easily converted to boronic acids by reaction with acid (Miyaura, N.; Suzuki, A. Chem., Rev., 1995, 95, pages 2457-2483). Thus a broad range of metallocenyl-containing pyridyl amine ligands may be readily prepared. Selected examples of metallocenylboronic acids and/or esters that may be of particular interest are shown below.

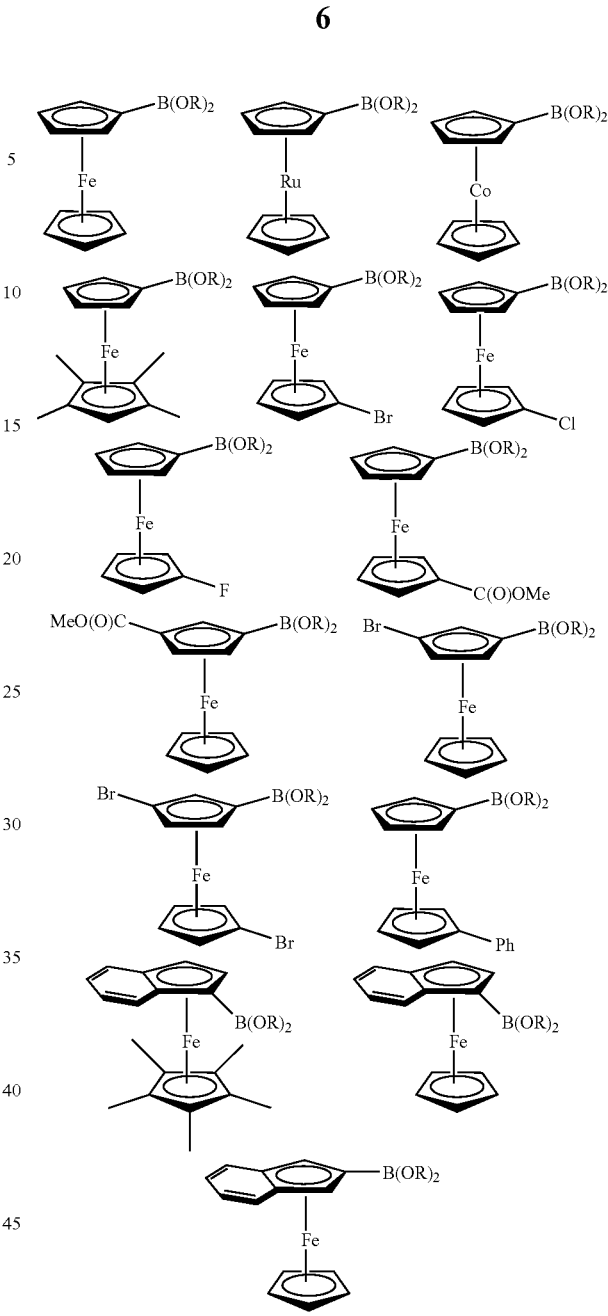

where Ph is phenyl, Me is methyl, and R is either hydrogen or an alkyl group, preferably a $C_1$ to $C_{10}$ alkyl group.

The second component for the metallocene-containing pyridyl amines is a pyridyl group. This may be coupled with the metallocenylboronic acid in the Pd-mediated reaction as described above. The pyridyl group desirably contains at least one pyridyl-halogen or similar bond that reacts with a reduced Pd species to form a Pd-pyridyl intermediate. This may be a Br or I group, although other groups (e.g., triflate) can be used. Some suitable pyridyl-containing materials that are commercially available are 6-bromo-2-pyridine carboxaldehyde (Sigma-Aldrich), 2,6-dibromopyrine (Sigma-Aldrich), and 2-acetyl-6-bromopyridine (Sigma-Aldrich). Pyridyl-containing groups of particular use for coupling with metallocenylboronic acids are tabulated below:

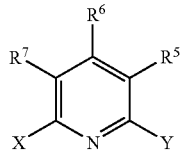

| X | R⁵ | R⁶ | R⁷ | Y |
|---|----|----|----|---|
| Br | H | H | H | Br |
| Br | H | H | H | C(O)Me |
| Br | H | H | H | CHO |
| Br | H | Me | H | CHO |
| Br | H | NMe₂ | H | CHO |
| Br | H | CF₃ | H | CHO |
| Br | H | Ph | H | CHO |
| Br | H | OMe | H | CHO |
| Br | H | F | H | CHO |
| Br | H | Cl | H | CHO |
| I | H | H | H | Br |
| I | H | H | H | C(O)Me |
| I | H | H | H | CHO |
| I | H | Me | H | CHO |
| I | H | NMe₂ | H | CHO |
| I | H | CF₃ | H | CHO |
| I | H | Ph | H | CHO |
| I | H | OMe | H | CHO |
| I | H | F | H | CHO |
| I | H | Cl | H | CHO | where Ph is phenyl and Me is methyl.

Using conventional synthesis techniques described in the Examples ligand precursors can be made having the structures set out below:

CHART 1

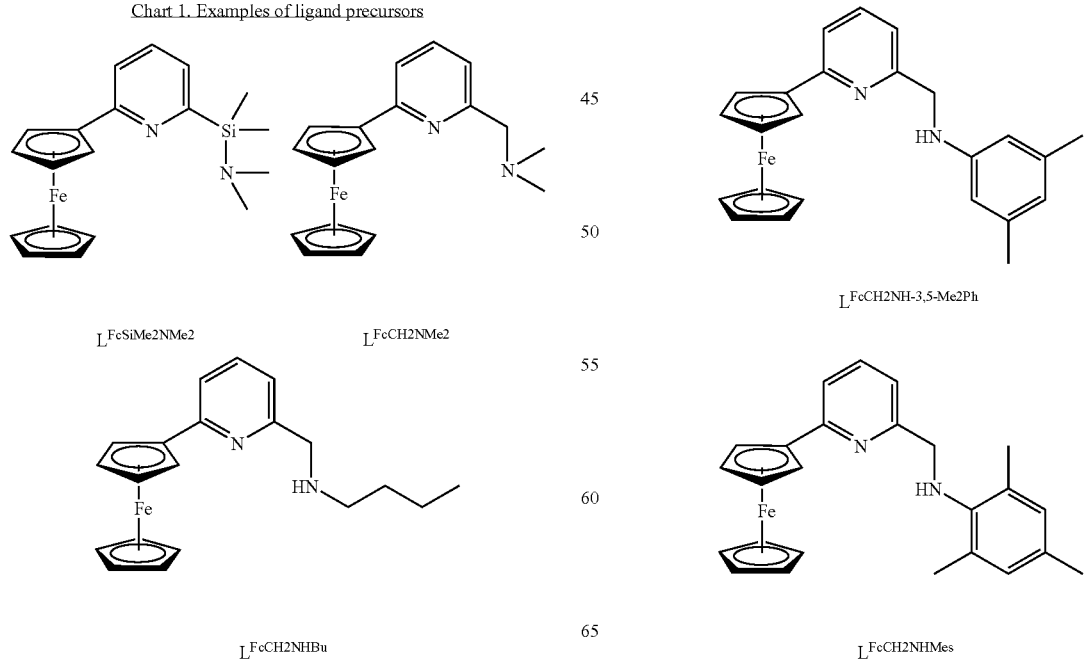

-continued

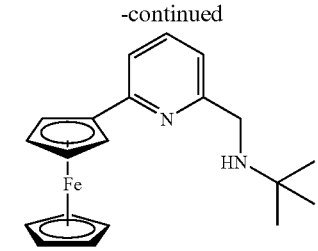

L$^{FcCH2NH-t-Bu}$

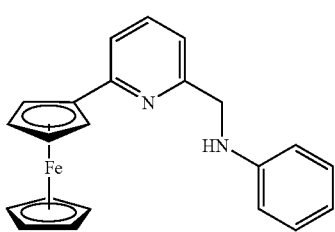

L$^{FcCH2NHPh}$

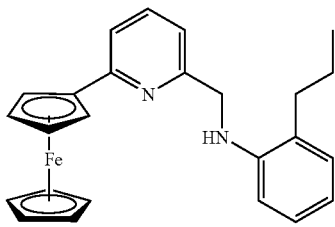

L$^{FcCH2NH(2-PrPh)}$

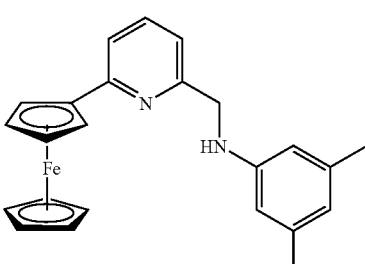

L$^{FcCH2NH-3,5-Me2Ph}$

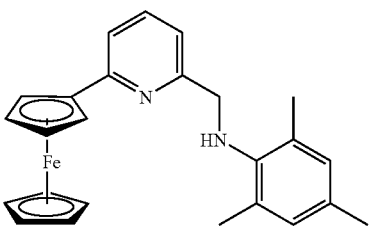

L$^{FcCH2NHMes}$

-continued

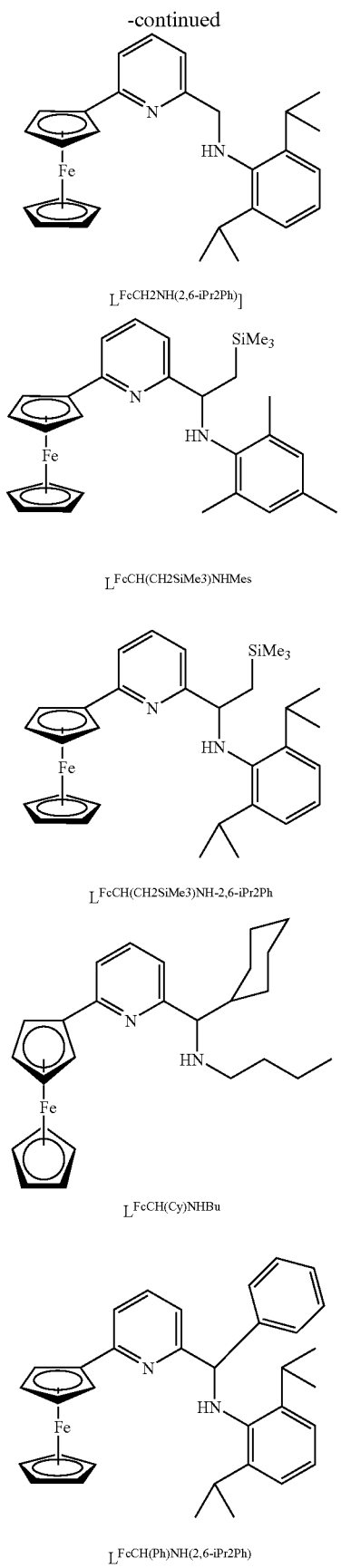

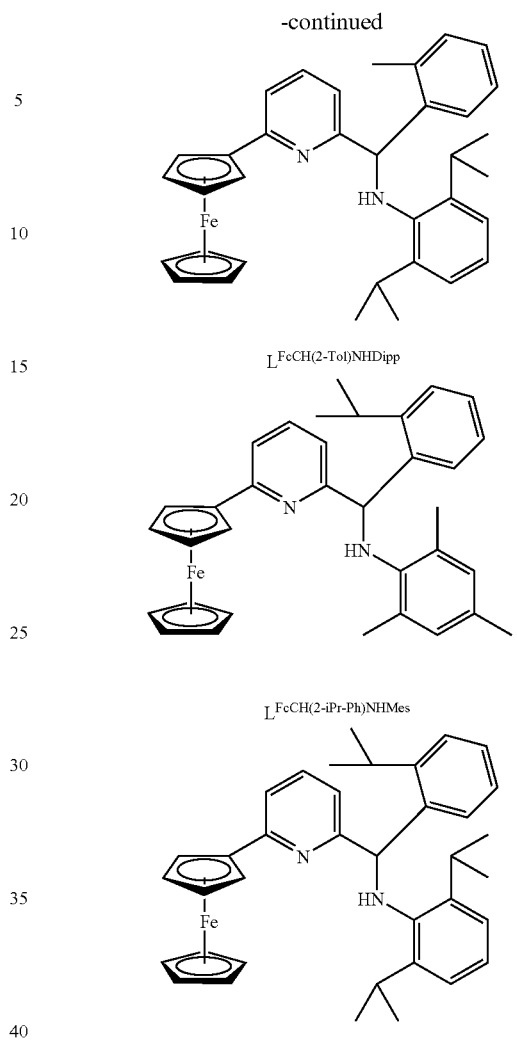

where Ph is phenyl, Me is methyl, Bu is butyl, t-Bu is tertiary-butyl, Mes is mesityl, PrPh is propylphenyl, iPr is isopropyl, Cy is cyclohexyl, Tol is toluoyl, and Dipp is diisopropylphenyl, and iPrPh is 2-isopropylphenyl.

The reactive ferrocenyl intermediates may be prepared by coupling a di-halo-pyridine with a ferrocenyl-based boronic acid to make a mono-halo-ferrocenyl pyridine. This can then be lithiated and reacted with an appropriate chlorosilane (e.g., $ClSiR^3R^4(NR^1R^2)$, where $R^1$, $R^2$, $R^3$, and $R^4$ are as defined above to obtain a silicon-bridged ferrocene-containing pyridylamine. Alternatively, the lithiated ferrocenyl intermediate may be reacted with $SiCl_2R^3R^4$, where $R^3$ and $R^4$ are as defined above), to form an intermediate which can be subsequently reacted with an amine or metalloamido reagent to form a silicon-bridged ferrocene-containing pyridylamine. Alternatively, also, the reactive ferrocenyl intermediates may be prepared by coupling a halo-pyridine-aldehyde or halo-pyridine-ketyl species with a ferrocene-based boronic acid. This route is useful to prepare ligand precursors that feature a carbon atom bridge. These can be reacted as described above with amine or metalloamido reagent to form a carbon-bridged ferrocene-containing pyridylamine.

The metal atom for $M^2$ is selected with a view to its intended use. Hafnium and zirconium are believed to be useful for olefin polymerization at higher temperatures; while chromium may be useful to create an oligomerization catalyst. Generally, ferrocenyl ligands can be readily incorporated. While not wishing to be bound by theory, it appears that the iron atom is not significantly affected by activation of $M^2$ so that the effect of the ferrocenyl group is to add bulk to the ligand. Additionally, metalation of the ferrocenyl group leads to a planar-chiral complex, which allows for the formation of $C_1$-symmetric metal complexes that are of interest as catalysts for stereo-controlled polymerizations.

Group 4 complexes prepared using ligands featuring sterically hindered Q and Z groups tend to yield the most active catalysts for ethylene-octene polymerization. Thus for these systems desirable groups for Q include —CH(2-toluoyl)- and —CH(2-isopropylphenyl)-. Desirable groups for —Z include 2,6-substituted arylamido groups such as —N(2,6-diisopropylphenyl). For Cr complexes for use in ethylene oligomerizations the highest activities were obtained for —Z being —NH-t-butyl.

The preparation of the transition metal complex involves the reaction of an organometallic transition metal reagent with the ligand precursor by different methods. One option is a protonolysis reaction between an amine ligand precursor and an organometallic reagent followed by transmetalation using a main-group alkylating reagent (if necessary). Another option involves an addition reaction of an imine ligand precursor with an organometallic reagent.

Exemplary transition metal complexes are set out in Chart 2.

CHART 2

Chart 2. Examples of ligand-metal complexes

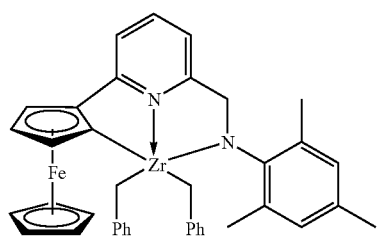

$[L^{FcCH2NMes}]ZrBn_2$

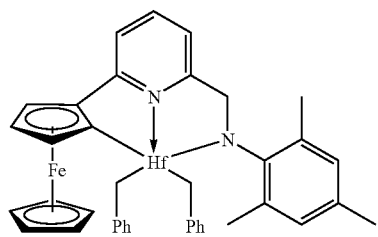

$[L^{FcCH2NMes}]HfBn_2$

-continued

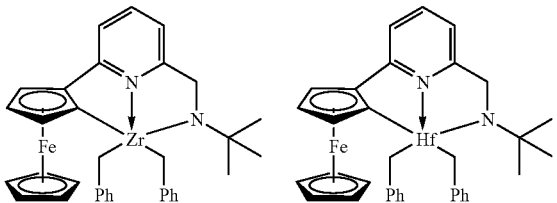

$[L^{FcCH2NtBu}]ZrBn_2$    $[L^{FcCH2NtBu}]HfBn_2$

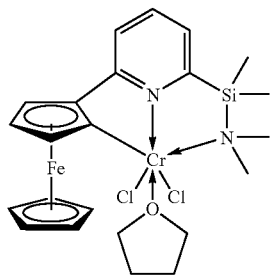

$[L^{FcSiMe2NMe2}]CrCl_2(thf)$

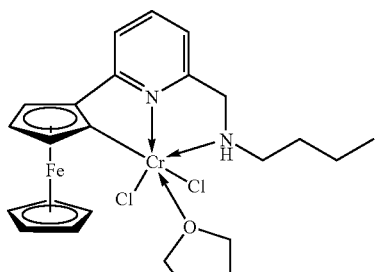

$[L^{FcCH2NHBu}]CrCl_2(thf)$

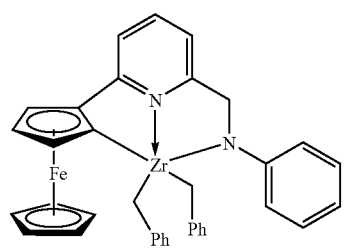

$[L^{FcCH2NPh}]ZrBn_2$

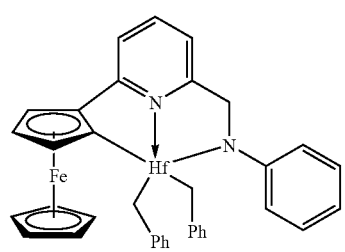

$[L^{FcCH2NPh}]HfBn_2$

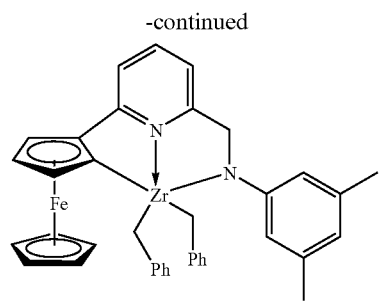
[L^{FcCH2N-3,5-Me2Ph}]ZrBn2
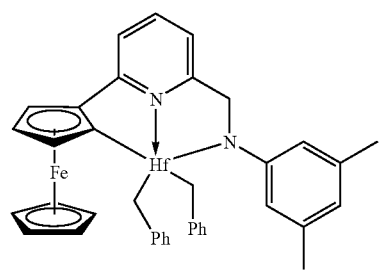
[L^{FcCH2N-3,5-Me2Ph}]HfBn2
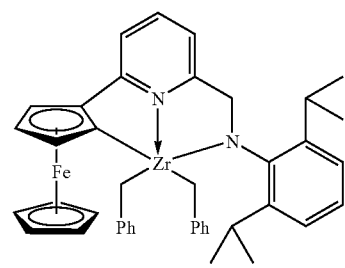
[L^{FcCH2NDipp}]ZrBn2
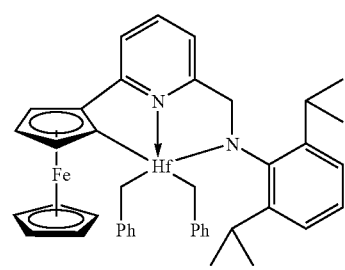
[L^{FcCH2NDipp}]HfBn2
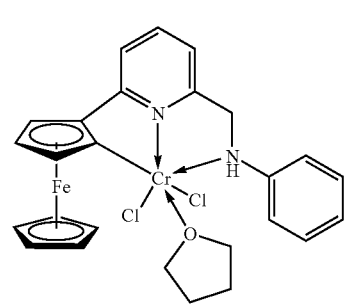
[L^{FcCH2NHPh}]CrCl2(thf)
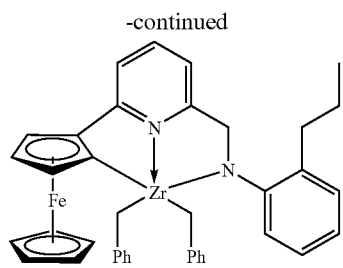
[L^{FcCH2N-2-PrPh}]ZrBn2
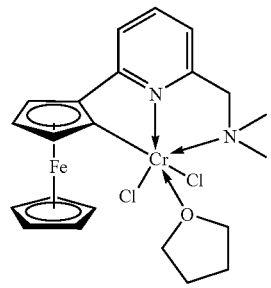
[L^{FcCH2NMe2}]CrCl2(thf)
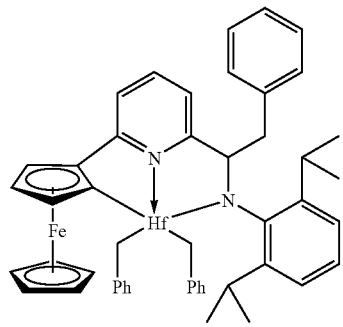
[L^{FcCH(Bn)NDipp}]HfBn2
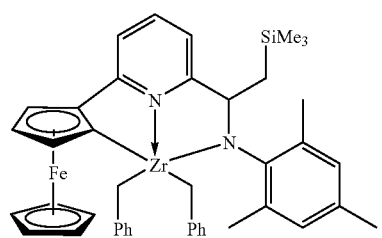
[L^{FcCH(CH2SiMe3)NDipp}]ZrBn2
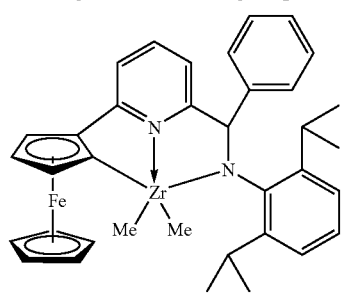
[L^{FcCH(Ph)NDipp}]ZrBn2

-continued
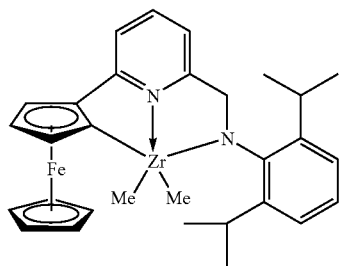
[L^{FcCH2NDipp}]ZrMe_2
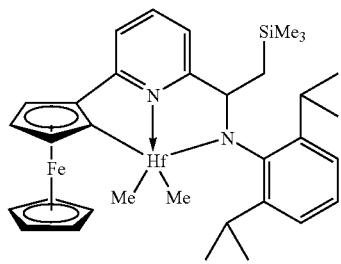
[L^{FcCH(CH2SiMe3)NDipp}]HfMe_2
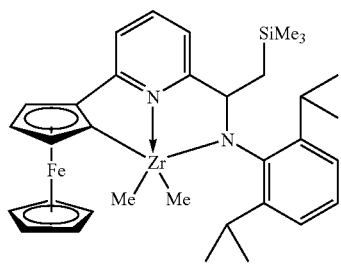
[L^{FcCH(CH2SiMe3)NDipp}]ZrMe_2
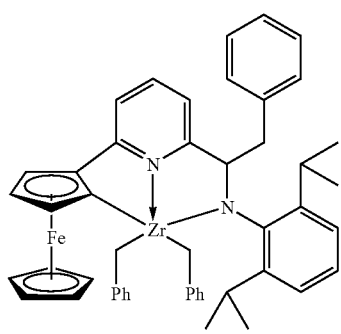
[L^{FcCH(Bn)NDipp}]ZrBn_2
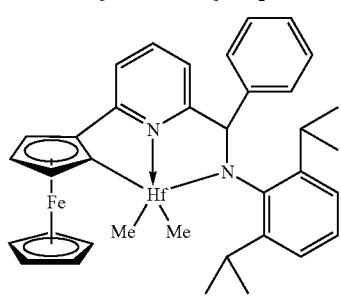
[L^{FcCH(Ph)NDipp}]HfMe_2
-continued
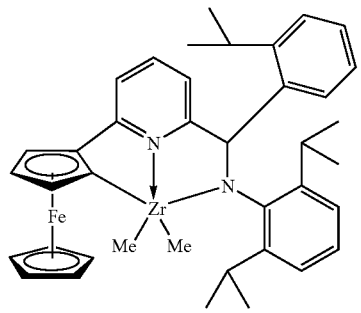
[L^{FcCH(2-iPrPh)NDipp}]ZrMe_2
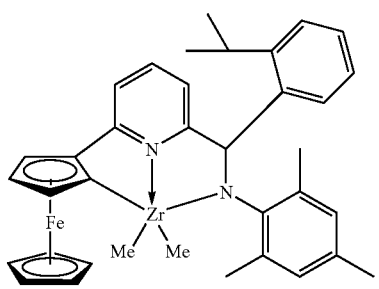
[L^{FcCH(2-iPrPh)NMes}]ZrMe_2
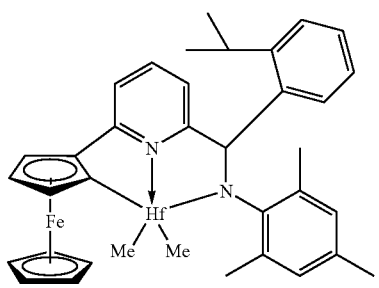
[L^{FcCH(2-iPrPh)NMes}]HfMe_2
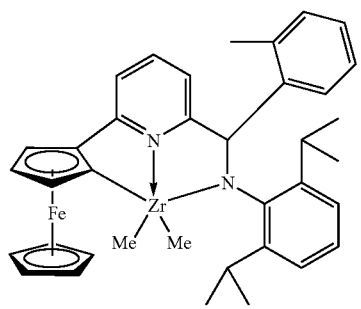
[L^{FcCH(2-Tol)NMes}]ZrMe_2

-continued

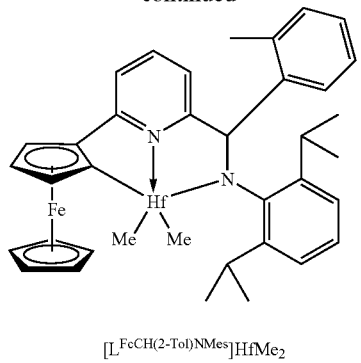

[L^{FcCH(2-Tol)NMes}]HfMe_2 where L is ligand, Fc is pyridyl-substituted ferrocene, Ph is phenyl, Me is methyl, Bu is butyl, t-Bu is tertiary-butyl, Mes is mesityl, PrPh is propyl-phenyl, iPr is isopropyl, iPPh is isopropyl-phenyl, Cy is cyclohexyl Tol is toluoyl, Dipp is di-isopropylphenyl, Bn is benzyl, and thf is tetrahydrofuran.

$M^2$ may be further substituted with a selection influenced by the selected system of activation. In the case of activation with a methyl alumoxane-based system the precursor groups may include leaving groups, such as, halogen that would be methylated in part in the polymerization process. Where the activation is through a non-coordinated anion in the absence of methylating reagents, any additional substitutions of $M^2$ are preferably with non-polar groups such as alkyls, etc.

Options for Reacting Ligands and Transition Metals

After the complexes have been synthesized, catalyst systems may be formed by combining them with activators in any of the manners known from the literature including by supporting them for use in slurry or gas phase polymerization. The catalyst systems may also be added to or generated in solution polymerization or bulk polymerization (in the monomer).

Oligomerization is defined herein as the combination of from 2 to 5 monomer units. This may be achieved while leaving terminal unsaturation so that the resulting oligomers can, if desired, take part in subsequent polymerization as a monomer. Polymerization is defined herein as the combination of sufficient monomer units to provide a number average molecular weight of at least 2000 g/mol as determined by GPC DRI.

The GPC procedure used in this and in later Tables is as follows. Weight average molecular weight (Mw) and number average molecular weight (Mn) were measured by GPC (Gel Permeation Chromatography) on a Waters 150 gel permeation chromatograph equipped with a differential refractive index (DRI) detector and Chromatix KMX-6 on line light scattering photometer. The system was used at 135° C. with 1,2,4-trichlorobenzene as the mobile phase. Shodex (Showa Denko America, Inc.) polystyrene gel columns 802, 803, 804, and 805 were used. Molecular weights are calibrated to polystyrene standards prepared by anionic, living polymerization. This technique is discussed in "Liquid Chromatography of Polymers and Related Materials III", J. Cazes, editor, Marcel Dekker, 1981, pg. 207, which is fully incorporated herein by reference. No corrections for column spreading were employed; however, data on generally accepted standards, e.g., National Bureau of Standards Polyethylene 1484 and anionically produced hydrogenated polyisoprenes (an alternating ethylene-propylene copolymer) demonstrated that such corrections on Mw/Mn (=MWD) were less than 0.05 units. Mw/Mn was calculated from elution times. The numerical analyses were performed using the commercially available Beckman/CIS customized LALLS software in conjunction with the standard Gel Permeation package. Solution NMR spectroscopic data were acquired on approximately 0.02 M solutions using a Bruker 250 MHz NMR spectrometer. Chemical shifts ($\delta$) for proton NMR spectra are given relative to residual protium in the deuterated solvent at $\delta$7.15, 7.24, 5.32, 3.58 (downfield methylene), and 2.09 ppm for $C_6D_6$, $CDCl_3$, $CD_2Cl_2$, $D_8$-thf, and $D_8$-toluene, respectively.

Activation may be performed using alumoxane solution supplied by Albemarle including methyl alumoxane, referred to as MAO, as well as modified MAO, referred to herein as MMAO, containing some higher alkyl groups to improve the solubility. MAO can be purchased from Albemarle in a 10 wt % solution in toluene.

Activation may also be performed using non-coordinated anions, referred to as NCA's, of the type described in EP 277 003 A1 and EP 277 004 A1. NCA may be added in the form of an ion pair using, for example, [DMAH]$^+$ [NCA]$^-$ in which the N,N-dimethylanilinium (DMAH) cation reacts with a basic leaving group on the transition metal complex to form a transition metal complex cation and [NCA]$^-$. The cation in the precursor may, alternatively, be trityl. Alternatively, the transition metal complex may be reacted with a neutral NCA precursor, such as $B(C_6F_5)_3$, which abstracts an anionic group from the complex to form an activated species. Useful activators include N,N-dimethylanilinium tetrakis(pentafluorophenyl)borate (i.e., [PhNMe$_2$H]B(C$_6$F$_5$)$_4$) and N,N-dimethylanilinium tetrakis(heptafluoronaphthyl)borate, where Ph is phenyl, and Me is methyl.

Polymerization may be homogeneous (solution or bulk polymerization) or heterogeneous (slurry in a liquid diluent) or gas phase (in a gaseous diluent). The polymerization is preferably continuous and uses an appropriately formulated catalyst system employing the transition metal complex. In the case of heterogeneous slurry or gas phase polymerization, the complex and activator may be supported by conventional methods. Silica is useful as a support herein.

Monomers useful herein include olefins having from 2 to 20 carbon atoms, alternately 2 to 10 carbon atoms (preferably ethylene, propylene, butylene, pentene, hexene, heptene, octene, nonene, and decene) and optionally also polyenes (such as dienes). Where olefins are used that give rise to short chain branching, such as propylene, the catalyst systems may, under appropriate conditions, generate stereoregular polymers or polymers having stereoregular sequences in the polymer chains. Particularly preferred monomers include ethylene, and mixtures of $C_2$ to $C_{10}$ alpha olefins, such as ethylene-propylene, ethylene-hexene, ethylene-octene, propylene-hexene, and the like.

In other embodiments, this invention relates to:

1. A compound represented by the formula:

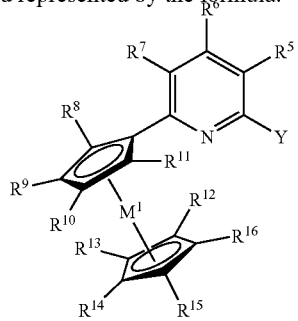

wherein $M^1$ is a metal atom selected from the group consisting of Fe, Ru, or Co; Y is a reactive moiety selected from the group consisting of —CHO, —C(O)R$^4$ or a halogen, and R$^4$ to R$^{16}$ can be independently selected from the group consisting of hydrogen, alkyl, aryl, arylalkyl, halogen, alkoxy, aryloxy, amino, silyl, and two adjacent carbon atoms of at least one cyclopentadienyl moiety may be linked by a saturated or unsaturated cyclic moiety having from 3 to 6 carbon atoms, optionally containing a heteroatom.

2. A compound for use as a ligand in a transition metal complex, the compound being represented by the formula:

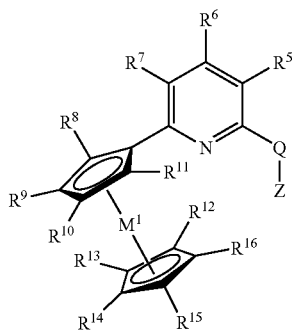

wherein $M^1$ is a metal atom selected from the group consisting of Fe, Ru, or Co; Q is $-CR^3R^4-$ or $-SiR^3R^4-$; and $R^1$ to $R^{16}$ can be independently selected from the group consisting of hydrogen, alkyl, aryl, arylalkyl, halogen, alkoxy, aryloxy, amino, silyl, Z is $-NR^1R^2$ or $=NR^2$ and two adjacent carbon atoms of at least one cyclopentadienyl moiety may be linked by a saturated or unsaturated cyclic moiety having from 3 to 6 carbon atoms, optionally containing a heteroatom, and $R^1$ and $R^2$ in $-NR^1R^2$ and $R^3$ and $R^4$ in $CR^3R^4-$ or $-SiR^3R^4$ may form a chain of from 3 to 6 carbon atoms, optionally including a heteroatom.

3. A transition metal complex represented by the formula:

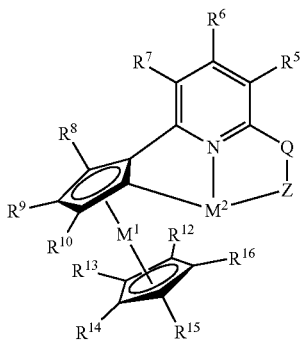

wherein $M^1$ is a metal atom selected from the group consisting of Fe, Ru, or Co; Q is $-CR^3R^4-$ or $-SiR^3R^4-$; Z is $-NR^1R^2$ or $-NR^2$ and $R^1$ to $R^{16}$ can be independently selected from the group consisting of hydrogen, alkyl, aryl, arylalkyl, halogen, alkoxy, aryloxy, amino, silyl and $M^2$ is a group 3 through group 6 metal with one to four additional donor and/or anionic ligands coordinated to $M^2$, and two adjacent carbon atoms of at least one cyclopentadienyl moiety may be linked by a saturated or unsaturated cyclic moiety having from 3 to 6 carbon atoms, optionally containing a heteroatom and $R^1$ and $R^2$ in $-NR^1R^2$ and $R^3$ and $R^4$ in $CR^3R^4-$ or $-SiR^3R^4$ may form a chain of from 3 to 6 carbon atoms, optionally including a heteroatom.

4. The complex according to paragraph 3 in which $M^2$ is a group 4 metal and Z is $-NR^2$ or $M^2$ is Cr and Z is $-NR^1R^2$.

5. The compound or complex according to any of paragraphs 1 to 4 in which $M^1$ is Fe or Ru and $R^8$ to $R_{16}$ are hydrogen.

6. The compound or complex according to according to any of paragraphs 1 to 5 in which the alkyl, aryl, arylalkyl, silyl, aryloxy and alkoxy moieties comprise from 1 to 20 carbon atoms and any alkylene moiety may be branched or linear.

7. A catalyst system comprising the reaction product of a complex according to any of paragraphs 3 to 6 and an activator selected from the group of alumoxane and non-coordinated anions.

8. A polymerization process which comprises contacting an olefin monomer with a catalyst system according to paragraph 7 in which the transition metal $M^2$ is selected from a group 4 transition metal and especially hafnium or zirconium.

9. An oligomerization process which comprises contacting olefin monomer with a catalyst system according to claim 7 in which the transition metal $M^2$ is chromium.

10. A process for producing a metallocenyl pyridine compound which comprises reacting a metallocenylboronic acid with a pyridyl compound containing at least one pyridyl-halogen or triflate group in the presence of a Pd catalyst, preferably 1,1'-bis(diphenylphosphino)ferrocene, and producing a compound represented by the formula:

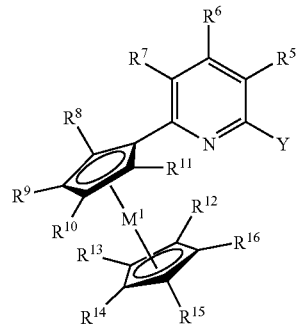

wherein $M^1$ is a metal atom selected from the group consisting of Fe, Ru, or Co; Y is a reactive moiety selected from the group consisting of $-CHO$, $-C(O)R^4$ or a halogen, and $R^4$ to $R^{16}$ can be independently selected from the group consisting of hydrogen, alkyl, aryl, arylalkyl, halogen, alkoxy, aryloxy, amino, silyl, and two adjacent carbon atoms of at least one cyclopentadienyl moiety may be linked by a saturated or unsaturated cyclic moiety having from 3 to 6 carbon atoms, optionally containing a heteroatom.

11. A process according to paragraph 10 which comprises coupling a di-halo-pyridine or a halo-pyridine-aldehyde or halo-pyridine-ketyl species with a metallocenyl-based boronic acid to produce an intermediate compound in which $-Y$ is halogen or $-CHO$ or $-C(O)R^4$.

12. A process according to paragraph 11 further comprising lithiating the compound in which $-Y$ is halogen and reacting the lithio product with a mono- or dichloro silicon derivative and, optionally, an amine or metal amido reagent, or reacting the compound in which $-Y$ is $-CHO$ or $-C(O)R^4$ with an amine and subsequently with an organometallic reagent to form a ligand precursor compound represented by the formula:

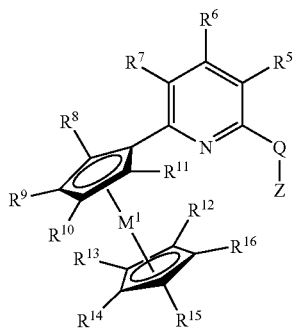

wherein M¹ is a metal atom selected from the group consisting of Fe, Ru, or Co; Q is —CR³R⁴— or —SiR³R⁴—; Z is —NR¹R² or =NR¹ and R¹ to R⁴ can be independently selected from the group consisting of hydrogen, alkyl, aryl, arylalkyl, halogen, alkoxy, aryloxy, amino, silyl, and two adjacent carbon atoms of at least one cyclopentadienyl moiety may be linked by a saturated or unsaturated cyclic moiety having from 3 to 6 carbon atoms, optionally containing a hetero-atom, and R¹ and R² in —NR¹R² and R³ and R⁴ in CR³R⁴— or —SiR³R⁴ may form a chain of from 3 to 6 carbon atoms, optionally including a heteroatom.

14. A process according to paragraph 13 which comprises subjecting the amine derivative produced to a protonolysis reaction between the ligand precursor and an organometallic reagent and then, optionally, alkylating the product by transmetalation or subjecting the imine derivative to an addition reaction of the imine ligand precursor with an organometallic reagent to produce a transition metal complex represented by the formula:

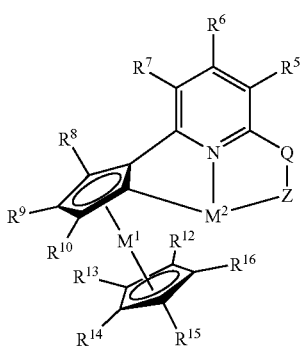

wherein M¹ is a metal atom selected from the group consisting Fe, Ru, or Co; Q is —CR³R⁴— or —SiR⁴R⁴—; and R¹ to R¹⁶ and Z are as indicated in the preceding claims, M² is a group 3 through group 6 metal (IUPAC standard periodic table) with one to four additional donor and/or anionic ligands coordinated to M², and two adjacent carbon atoms of at least one cyclopentadienyl moiety may be linked by a saturated or unsaturated cyclic moiety having from 3 to 6 carbon atoms, optionally containing a heteroatom.

EXAMPLES

The following abbreviations are used in the Examples: Ph is phenyl, Me is methyl, Bu is butyl, t-Bu is tertiary-butyl, Mes is mesityl, PrPh is propylphenyl, iPr is isopropyl, iPrPh is isopropylphenyl, Cy is cyclohexyl, Tol is toluoyl, tol is toluoyl, Dipp is di-isopropylphenyl, Bn is benzyl, THF is tetrahydrofuran, thf is tetrahydrofuran, dppf=1,1'-bis(diphenylphosphino)ferrocene. The chemical compositions of the ligand abbreviations used (e.g., $L^{FcCH2NHDipp}$) are shown in Charts 1 and 2. These abbreviations are not intended to be accurate chemical formulas, but instead present some useful information in a convenient manner.

Synthesis of Ligand Precursors

Ligand precursors are prepared using two different routes (methods A and B). Each route employs a key intermediate species (intermediates I-A and I-B). Method A is particularly useful for the preparation of ligand precursors that have Q=alkyl bridge. Method B can be used for the preparation of ligand precursors that have Q=silyl bridge or others. The two ligand precursor syntheses that follow demonstrate these two methods.

Synthesis of 6-ferrocenyl-2-pyridinecarboxaldehyde (I-A). See Scheme 1. Toluene (500 mL) was added to a mixture of 2-bromo-6-pyridinecarboxaldehyde (16.25 g, 87.36 mmol, purchased from Sigma-Aldrich), ferrocenylboronic acid (24.10 g, 104.9 mmol, purchased from Sigma-Aldrich), and (dppf)PdCl₂.CH₂Cl₂ (2.14 g, 2.62 mmol, purchased from Strem), under a nitrogen atmosphere. Then a nitrogen-sparged solution of Na₂CO₃ (210 mL, 210 mmol) in 4:1 water:methanol was added. The biphasic mixture was heated to 60° C. After 1 hour, the solution was heated to 80° C. for one week. The mixture was then filtered and the organics were separated and dried over MgSO₄. Evaporation yielded the crude 6-ferrocenyl-2-pyridinecarboxaldehyde which was purified on SiO₂ using 3:1 to 4:1 CH₂Cl₂:hexane as the elutant. Yield: 6.02 g, 23.7%. ¹H NMR (C₆D₆): δ 10.18 (1H, s), 7.58 (1H, d), 8.03-6.85 (2H, m), 4.91 (2H, m), 4.20 (2H, m), 3.86 (5H, s).

Synthesis of $L^{FcCH2NHMes}$, See Scheme 2. Tetrahydrofuran (20 mL), I-A (0.800 g, 2.75 mmol), and 3 angstrom molecular sieves were combined. Then 2,4,6-trimethylaniline (0.372 g, 2.75 mmol) was added and the flask was sealed. After heating to 70° C. overnight p-toluenesulfonic acid monohydrate (0.026 g, 0.14 mmol) was added and the mixture was heated to 70° C. for 1 hour. The mixture was then cooled to ambient temperature and LiAlH₄ (0.24 g, 6.3 mmol) dissolved in tetrahydrofuran (5 mL) was added dropwise. After 40 minutes water (2 mL) was added. Removal of volatiles afforded the crude product which was purified on a SiO₂ column using 20:1 CH₂Cl₂:EtOAc as the elutant. Yield of $L^{FCCH2NHMes}$: 0.50 g, 44%. ¹H NMR (C₆D₆): δ 7.06-6.94 (2H, m), 6.83 (2H, s), 6.60 (1H, dd, J=7, 1.5 Hz), 4.97 (2H, t, J=2 Hz), 4.70 (1H, br s), 4.22 (2H, br s), 4.30 (2H, t, J=2 Hz), 3.93 (5H, s), 2.38 (6H, s), 2.21 (3H, s). Scheme 1 is a preliminary coupling reaction, where 7d is 7 days. Step 1 in Scheme 2 is an addition-condensation reaction with the reactive CHO group and step 2 of Scheme 2 is a reduction to the amine, where p-tolSO₃H is para-toluenesulfonic acid.

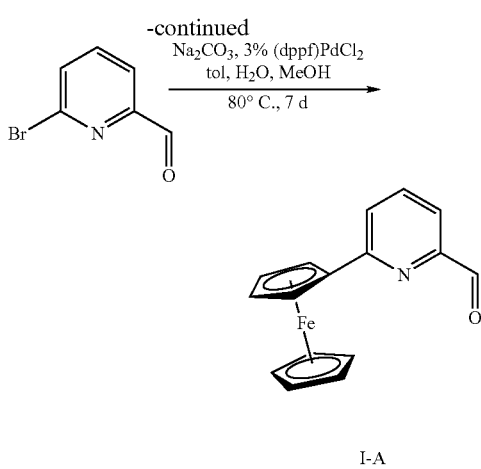

was isolated by crystallization from hexamethyldisiloxane. Yield: 0.058 g (12%). $^1$H NMR($C_6D_6$): δ 6.87 (1H, d), 6.79 (1H, d), 6.64 (1H, t), 4.83 (2H, m), 4.11 (2H, m), 3.83 (5H, s).

Synthesis of $L^{FcSiMe2NMe2}$ See Scheme 4. Tetrahydrofuran (15 mL) was added to I-A (0.039 g, 0.114 mmol) to form a clear orange solution. At −80° C. a hexane solution of BuLi (0.0483 mL, 0.113 mmol) was added to form a clear orange solution. After 15 min. a cold tetrahydrofuran solution (2 mL) of $Me_2SiCl(NMe_2)$ (0.068 g, 0.490 mmol, prepared as described by Washburne et al., J. Organomet. Chem., 1970, 21, pages 59-64) was added in one portion. The solution was allowed to warm slowly to ambient temperature. After several hours the volatiles were removed to afford a residue that was extracted with hexane (3 mL) and filtered. Removal of the volatiles afforded $L^{FCSiMe2NMe2}$ as an orange oily solid. Yield: 0.023 g, 55%. $^1$H NMR($C_6D_6$): δ 7.2-7.0 (3H, m), 4.99 (2H, m), 4.21 (2H, m), 3.93 (5H, s), 2.58 (6H, s), 0.48 (6H, m). Item number 1 in Scheme 4 represents a lithium-halogen exchange reaction.

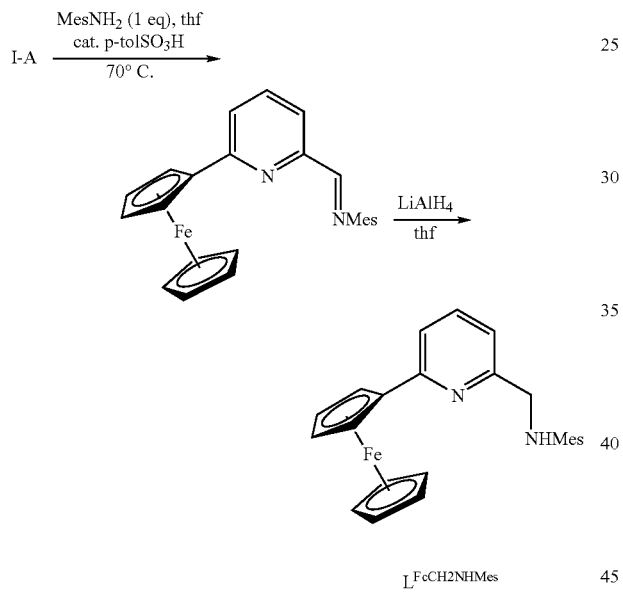

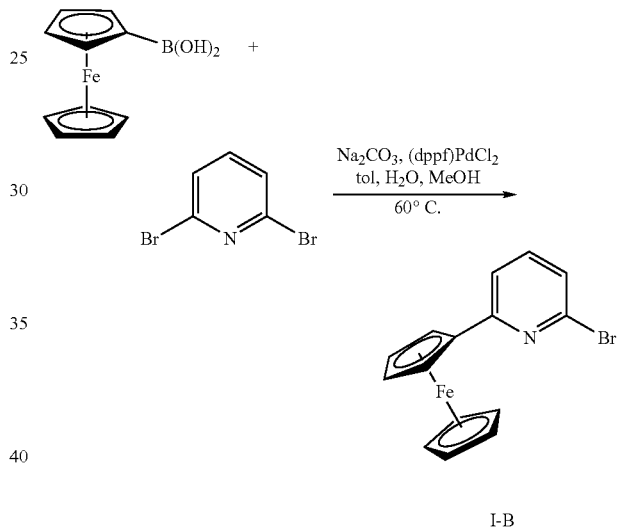

Synthesis of 2-bromo-6-ferrocenylpyridine (I-B). See Scheme 3. Toluene (15 mL) was added to 2,6-dibromopyridine (0.341 g, 1.44 mmol, purchased from Sigma-Aldrich) and ferrocenylboronic acid (0.321 g, 1.40 mmol, purchased from Sigma-Aldrich) to form an orange suspension. A suspension of $(dppf)PdCl_2 \cdot CH_2Cl_2$ (0.047 g, 0.058 mmol, purchased from Strem) (dppf=1,1'-bis(diphenylphosphino)ferrocene) in toluene (5 mL) was then added followed by a 1 M solution of $Na_2CO_3$ (10 mL, 10 mmol) in 4:1 water:methanol. The biphasic mixture was heated to 60° C. for 23 hours. At this time $^1$H NMR spectroscopic analysis indicated approximately 45% conversion to the desired product. The organic layer was separated, washed with a little water and then brine. The organics were then dried over $MgSO_4$ and filtered. Removal of the volatiles afforded an orange residue. The remaining 2,6-dibromopyridine was removed by sublimation at 45° C./ca. 100 mTorr over 2 hours. The crude was purified on an $Al_2O_3$ column using 4% ethyl acetate in hexane as the elutant. The product was still contaminated with some 2,6-diferrocenylpyridine. Pure 2-bromo-6-ferrocenylpyridine

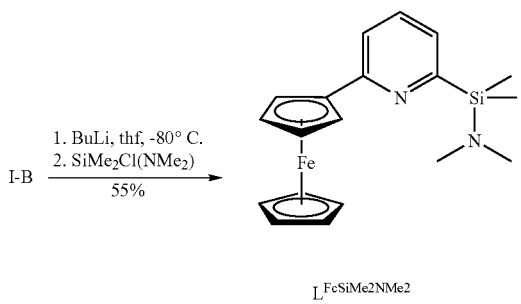

Synthesis of Ligand-Metal Complexes

Figure 2:
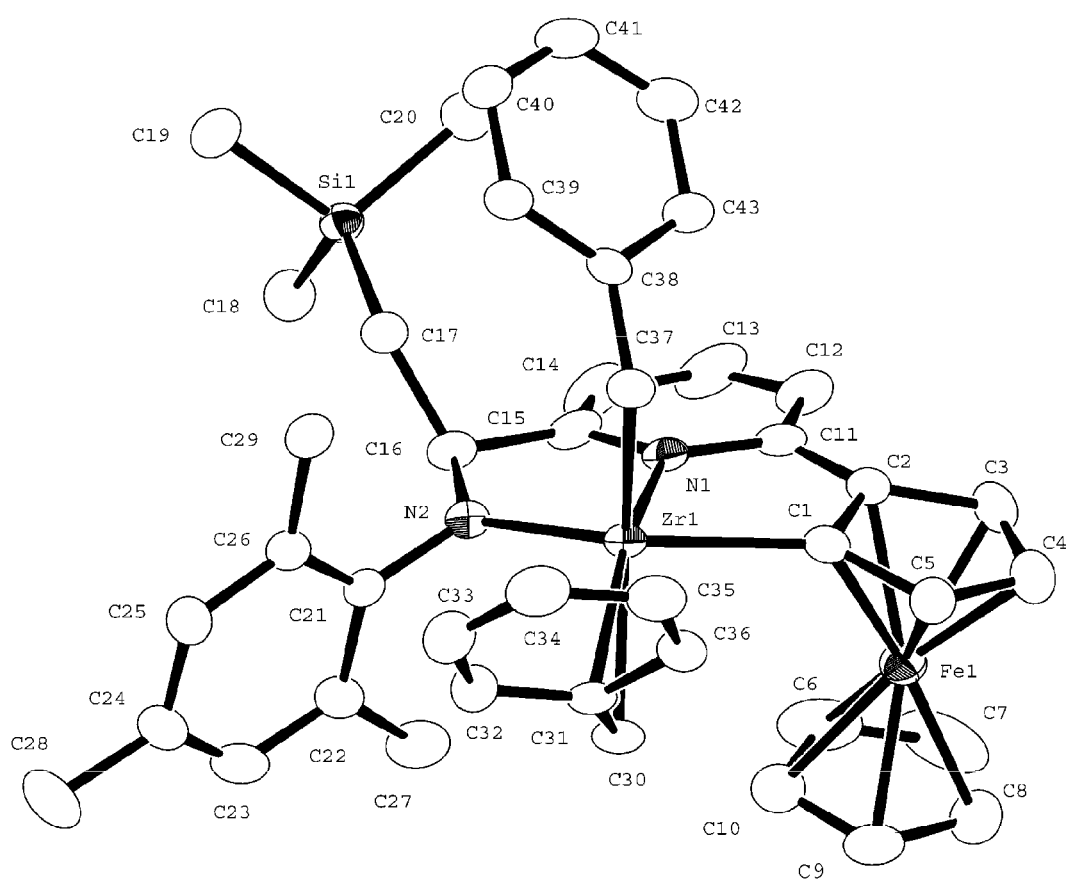
FIG. 2 is an illustration of the molecular structure of $[L^{FcCH(CH2SiMe3)NMes}]ZrBn_2$ as determined by single-crystal X-ray diffraction.
Figure 3:
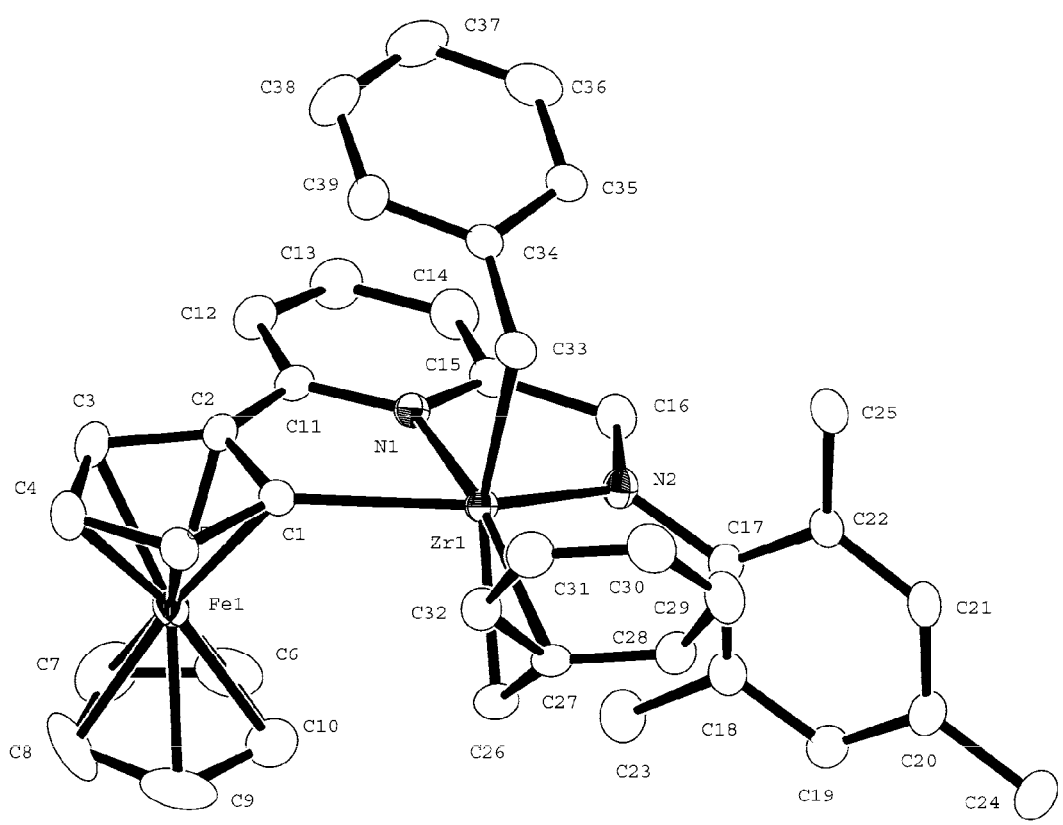
FIG. 3 is an illustration of the molecular structure of $[L^{FcCH2NMes}]ZrBn_2$ as determined by single-crystal X-ray diffraction.
Figure 4:
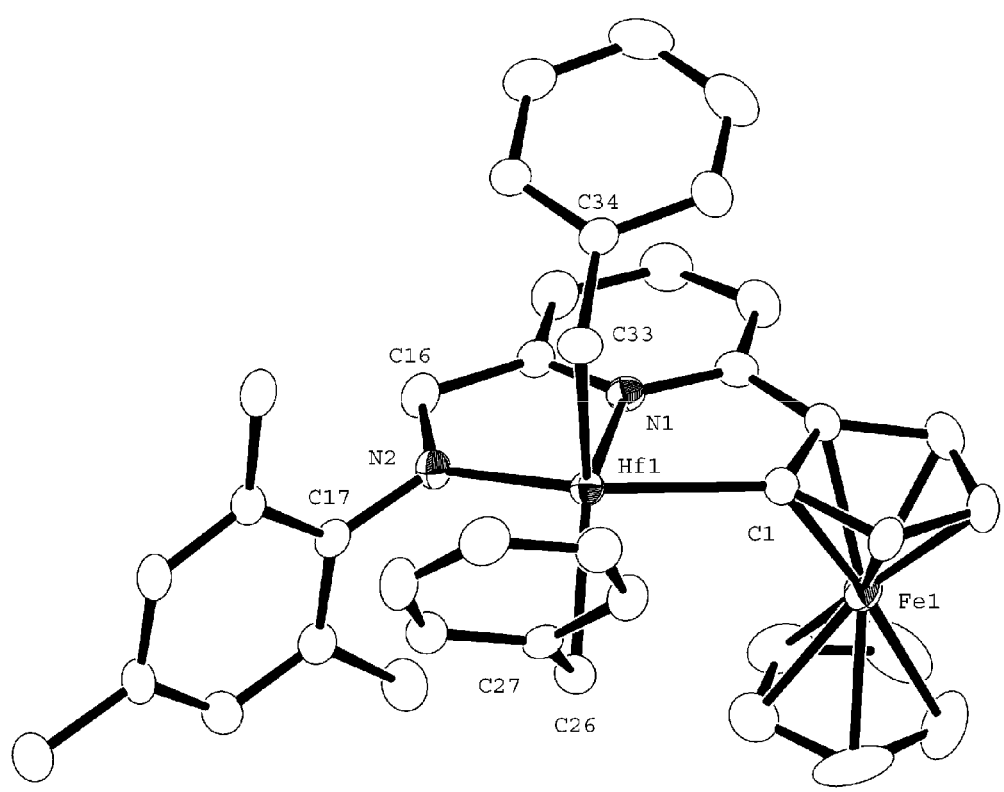
FIG. 4 is an illustration of the molecular structure of $[L^{FcCH2NMes}]HfBn_2$ as determined by single-crystal X-ray diffraction.
Figure 5:
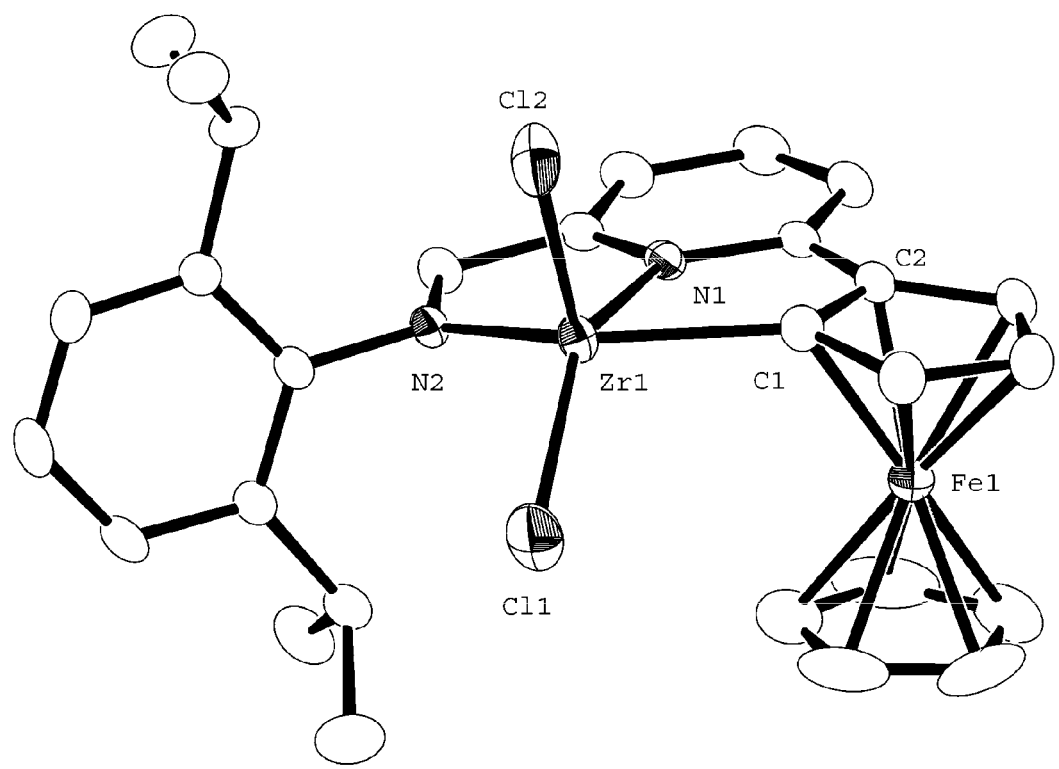
FIG. 5 is an illustration of the molecular structure of $[L^{FcCH2NDipp}]ZrCl_2$ as determined by single-crystal X-ray diffraction.
Figure 6:
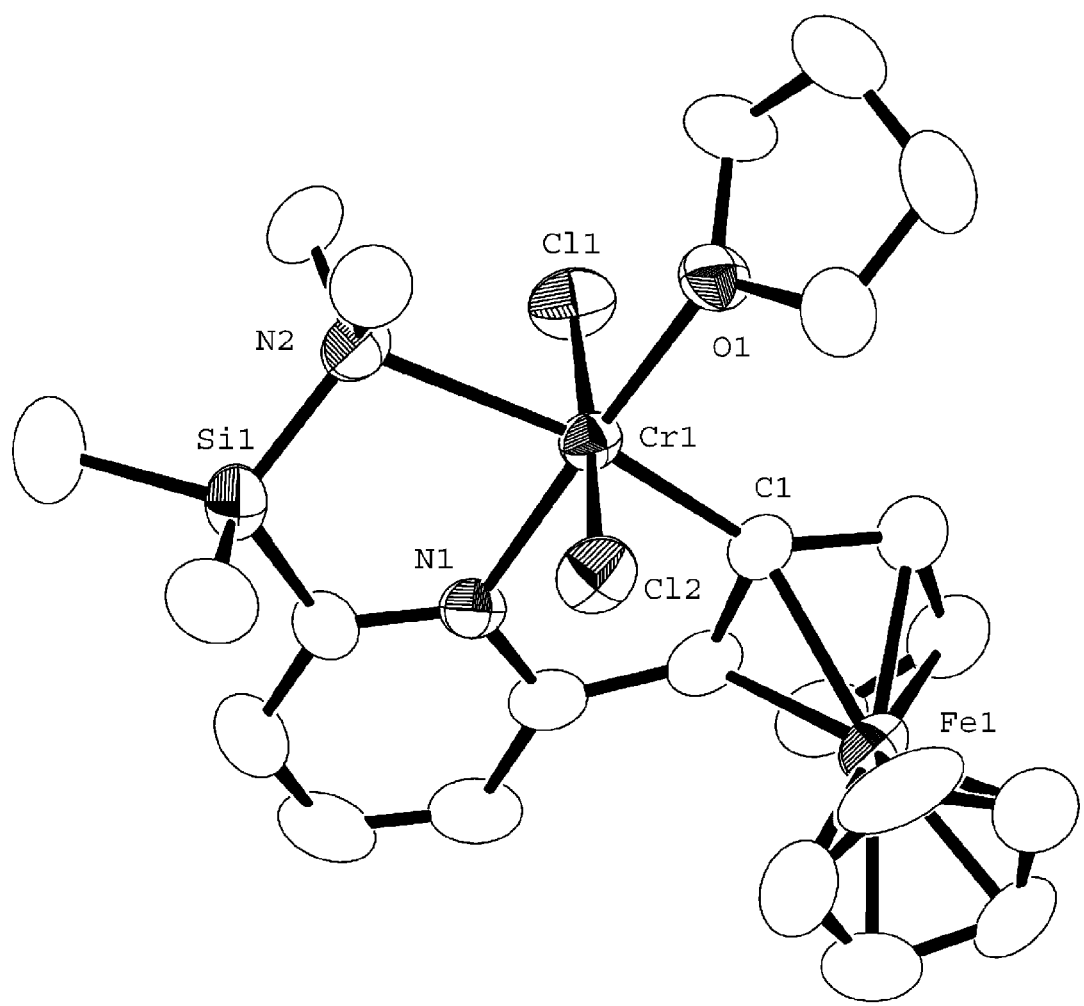
FIG. 6 is an illustration of the molecular structure of $[L^{FeSiMe2NMe2}]CrCl_2(thf)$ as determined by single-crystal X-ray diffraction.

Metal-ligand complexes have been prepared using two different methods. These are method C, which involves a protonolysis reaction between an amine ligand precursor and an organometallic reagent followed by transmetalation using a main-group alkylating reagent (if necessary), and method D, which involves an addition reaction of an imine ligand precursor with an organometallic reagent. These two methods are exemplified by the four following experimental descriptions. Six ligand-metal complexes have been characterized using single-crystal X-ray diffraction. The molecular structures are shown in FIGS. 1 to 6.

Synthesis of $[L^{FcCH2NMes}]Zr(CH_2Ph)_2$ as an example of method C. See Scheme 5. Solid $Zr(CH_2Ph)_4$ (0.994 g, 0.218 mmol) was added to a toluene (6 mL) solution of $L^{FcCH2NMes}$ (0.0895 g, 0.218 mmol). The clear orange solution was heated to 50° C. for 6 hours in the dark. The volatiles were then removed from the red solution to afford a red residue that was crystallized from $Et_2O$ at −35° C. to give red crystals. Yield: 0.080 g, 54%. $^1$H NMR ($C_6D_6$, 500 MHz): δ 7.18 (2H, t, J=7.5 Hz), 7.05 (1H, t, J=7.5 Hz), 6.95 (1H, br), 6.89 (1H, br), 6.83 (1H, t, J=7.8 Hz), 6.71 (2H, d, J=8.5 Hz), 6.65 (2H, t, J=7.8 Hz), 6.54 (2H, d, J=7.0 Hz), 6.47 (1H, 7.5 Hz), 4.71 (d, 1H, J=20.0 Hz), 4.49 (1H, m), 4.47 (1H, m), 4.43 (1H, m), 4.25 (1H, d, J=20.0 Hz), 2.96 (1H, d, J=8.0 Hz), 2.41 (3H, s), 2.30 (3H, s), 2.23 (1H, d, 8.0 Hz), 2.20 (3H, s), 1.58 (2H, AB quartet, Δν=35.5 Hz, J=11 Hz).

Scheme 5

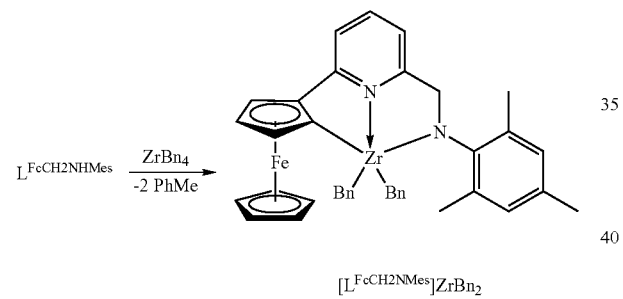

[$L^{FcCH2NMes}$]ZrBn$_2$

Scheme 6

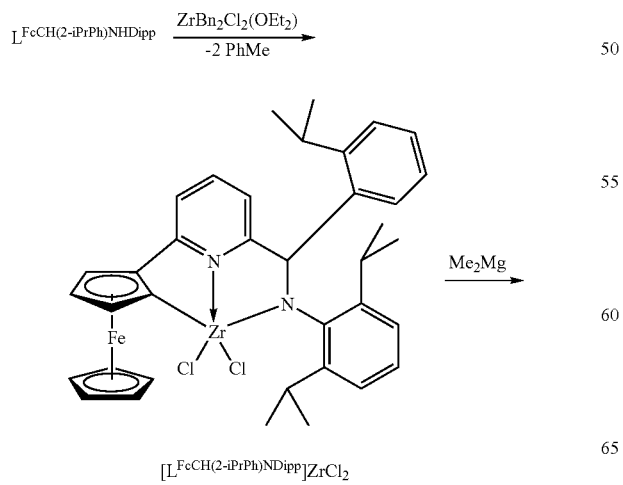

[$L^{FcCH(2-iPrPh)NDipp}$]ZrCl$_2$

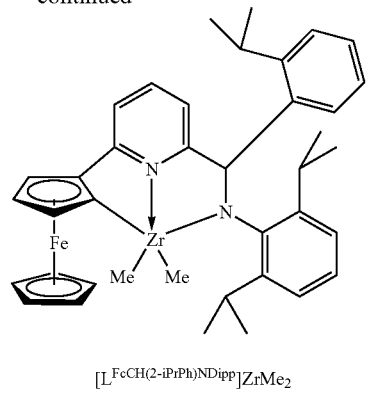

[$L^{FcCH(2-iPrPh)NDipp}$]ZrMe$_2$

Scheme 7

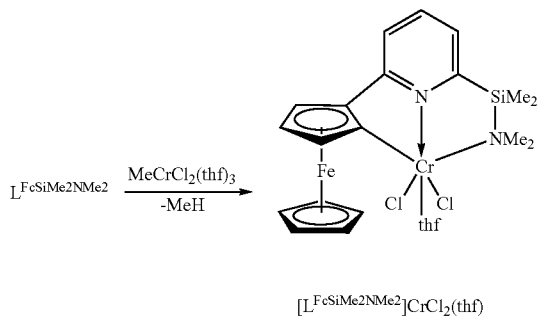

[$L^{FcSiMe2NMe2}$]CrCl$_2$(thf)

Scheme 8

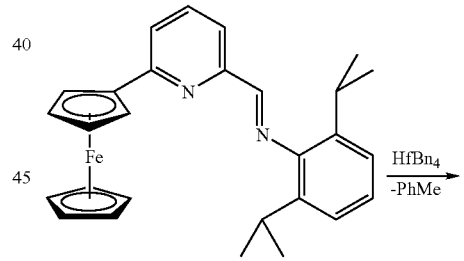

$L^{FcCH=NDipp}$

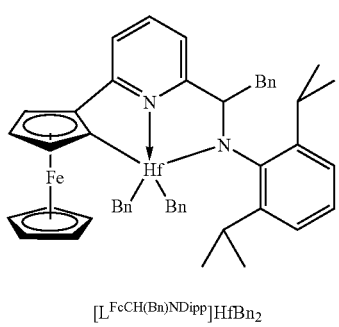

[$L^{FcCH(Bn)NDipp}$]HfBn$_2$

Synthesis of $[L^{FcCH(2-iPrPh)NDipp}]ZrMe_2$ as an example of method C. See Scheme 6. Benzene (5 mL) was added to $L^{FcCH(2-iPrPh)NDipp}$ (0.085 g, 0.15 mmol) and $ZrBn_2Cl_2$ (OEt$_2$) (0.062 g, 0.15 mmol) to form a clear red solution. The mixture was stirred for 1.5 hours and then heated to 70° C. for 2 hours. The volatiles were removed to afford a dark residue. Then Et$_2$O (4 mL) was added followed by the dropwise addition of Et$_2$O solution of Me$_2$Mg (1.0 mL, 0.16 mmol). After 1 hour the volatiles were removed and the residue was extracted with benzene. Filtration, concentration, and the addition of some Et$_2$O led to the precipitation of the product as an orange solid (0.036 g, 35%). $^1$H NMR spectroscopic analysis indicated that the product was a 9:2 mixture of two diastereoisomers. $^1$H NMR (C$_6$D$_6$): selected resonances for major diastereoisomer, 6.22 (1H, s, —CH(Ar)N—), 4.90 (1H, m, CpH), 4.61 (1H, t, CpH), 4.57 (1H, m, CpH), 4.08 (5H, s, CpH), 1.41 (3H, s, ZrMe), 0.84 (3H, ZrMe). Synthesis of [L$^{FcSiMe2NMe2}$]CrCl$_2$(thf) as an example of method C. See Scheme 7. Toluene (3 mL) was added to L$^{FcSiMe2NMe2}$ (0.020 g, 0.055 mmol) to form a clear orange solution. Solid CrMeCl$_2$(thf)$_3$ (0.019 g, 0.054 mmol) was then added and the mixture was heated to 60° C. The solution darkened quickly and after 10 min dark precipitate had formed. The precipitate was collected, washed with toluene, and dried under reduced pressure. Yield: ca. 0.020 g, 65%. The solid was then crystallized to form a 1:2 thf-hexane solution (5 mL). Analysis by single-crystal X-ray diffraction confirmed the identity of the product. XRD data (see FIG. 2): a=11.237 (4), b=18.566 (6), c=12.372 (4), β=91.051 (8), V=2580(2), P2(1)/c (#14), FeCrClSiON$_2$C$_{23}$H$_{32}$, Z=4, observations=5831, variables=281, R1 (I>2σI)=0.0673, wR2 (all)=0.1156, GOF=1.100, peak=0.35, hole=−0.30.

Synthesis of [L$^{FcCH(Bn)NDipp}$]HfBn$_2$ as an example of method D. See Scheme 8. Toluene (4 mL) was added to HfBn$_4$ (0.094 g, 0.173 mmol) to form a clear yellow solution. At −80° C., a toluene solution (2 mL) of the imine LFcCH=NDipp (0.078 g, 0.173 mmol) (the imine was prepared from 2,6-diisopropylaniline and 6-ferrocenyl-2-pyridinecarboxaldehyde using the procedure described earlier) was added dropwise over 10 minutes. The deep red solution was allowed to slowly warm to ambient temperature over 5 hours. Stirred overnight and then the volatiles were removed to afford a red oil. Addition of hexane (6 mL) and cooling to −35° C. afforded the product as red crystals (0.050 g, 30%). $^1$H NMR spectroscopic data indicates that the isolated product is a 3:2 mixture of diastereoisomers. $^1$H NMR (C$_6$D$_6$): δ selected resonances for major diastereoisomer, 5.36 (1H, dd, —CH(Bn)N—), 4.59 (1H, t, CpH), 4.51 (1H, t, CpH), 4.44 (1H, t, CpH), 4.03 (5H, s, CpH); selected resonances for minor diastereoisomer, 4.82 (1H, dd, —CH(Bn)N—), 4.59 (1H, t, CpH), 4.52 (1H, t, CpH), 4.44 (1H, t, CpH), 3.92 (5H, s, CpH).

Example Polymerization of Activated Complexes with Ethylene-octene Mixtures

Transition metal complexes of ferrocene-containing pyridyl amine ligands, when mixed with activators, were found to react with ethylene-octene mixtures to form polymers. In some cases highly active catalysts were formed. Selected results of different runs are shown in Table 1. Specific reaction conditions are given as a footnote in the table. Reactions were performed in a 48-well parallel pressure reactor which is described in WO 00/09255, U.S. Pat. Nos. 6,306,658; 6,455,316; 6,489,168; and J. Am. Chem. Soc., 2003, 125, pg. 4306.

TABLE 1

Primary catalyst screening data for ethylene-octene copolymerization.*

| run | Catalyst | Activator | T (° C.) | Activity | wt % C8 | Mw | Mn | Mw/Mn |
|---|---|---|---|---|---|---|---|---|
| 1 | [L$^{FcCH(Bn)NDipp}$]ZrBn$_2$ | [PhNMe$_2$H]B(C$_6$F$_5$)$_4$ | 50 | 702 | 1 | 3,729,685 | 1,904,253 | 2 |
| 2 | [L$^{FcCH(Bn)NDipp}$]ZrBn$_2$ | [PhNMe$_2$H]B(C$_6$F$_5$)$_4$ | 80 | 45 | 2 | 3,712,291 | 2,145,446 | 1.7 |
| 3 | [L$^{FcCH(Bn)NDipp}$]ZrBn$_2$ | MAO | 50 | 396 | 1 | 135,594 | 86,231 | 1.6 |
| 4 | [L$^{FcCH(Bn)NDipp}$]ZrBn$_2$ | MAO | 80 | 55 | 1 | 244,690 | 61,265 | 4 |
| 5 | [L$^{FcCH(2-iPrPh)NDipp}$]ZrMe$_2$ | [PhNMe$_2$H]B(C$_6$F$_5$)$_4$ | 70 | 110 | 2 | 1,744,446 | 808,882 | 2.2 |
| 6 | [L$^{FcCH(2-iPrPh)NDipp}$]ZrMe$_2$ | [PhNMe$_2$H]B(C$_6$F$_5$)$_4$ | 80 | 65 | 2 | 2,004,175 | 1,038,940 | 1.9 |
| 7 | [L$^{FcCH(2-iPrPh)NDipp}$]ZrMe$_2$ | [PhNMe$_2$H]B(C$_6$F$_5$)$_4$ | 90 | 47 | 2 | 1,902,841 | 1,091,269 | 1.7 |
| 8 | [L$^{FcCH(2-iPrPh)NDipp}$]ZrMe$_2$ | [PhNMe$_2$H]B(C$_6$F$_5$)$_4$ | 110 | 47 | 3 | 1,747,900 | 553,393 | 3.2 |
| 9 | [L$^{FcCH(2-iPrPh)NDipp}$]ZrMe$_2$ | MAO | 50 | 1466 | 2 | 137,068 | 86,364 | 1.6 |
| 10 | [L$^{FcCH(2-iPrPh)NDipp}$]ZrMe$_2$ | MAO | 70 | 6481 | 3 | 121,944 | 81,768 | 1.5 |
| 11 | [L$^{FcCH(2-iPrPh)NDipp}$]ZrMe$_2$ | MAO | 80 | 4880 | 3 | 96,799 | 60,697 | 1.6 |
| 12 | [L$^{FcCH(2-iPrPh)NDipp}$]ZrMe$_2$ | MAO | 90 | 3353 | 2 | 87,574 | 57,816 | 1.5 |
| 13 | [L$^{FcCH(2-Tol)NDipp}$]ZrMe$_2$ | [PhNMe$_2$H]B(C$_6$F$_5$)$_4$ | 50 | 7 | n.d. | n.d. | n.d. | n.d. |
| 14 | [L$^{FcCH(2-Tol)NDipp}$]ZrMe$_2$ | [PhNMe$_2$H]B(C$_6$F$_5$)$_4$ | 80 | 40 | 3 | 1,847,840 | 965,502 | 1.9 |
| 15 | [L$^{FcCH(2-Tol)NDipp}$]ZrMe$_2$ | MAO | 50 | 3005 | 3 | 133,902 | 87,366 | 1.5 |
| 16 | [L$^{FcCH(2-Tol)NDipp}$]ZrMe$_2$ | MAO | 80 | 4540 | 3 | 94,171 | 64,121 | 1.5 |
| 17 | [L$^{FcCH(Bn)NDipp}$]HfBn$_2$ | [PhNMe$_2$H]B(C$_6$F$_5$)$_4$ | 50 | 345 | n.d. | n.d. | n.d. | n.d. |
| 18 | [L$^{FcCH(Bn)NDipp}$]HfBn$_2$ | [PhNMe$_2$H]B(C$_6$F$_5$)$_4$ | 80 | 25 | 4 | 1,973,540 | 639,628 | 3.1 |
| 19 | [L$^{FcCH(Bn)NDipp}$]HfBn$_2$ | MAO | 50 | 38 | 2 | 364,869 | 17,687 | 20.6 |
| 20 | [L$^{FcCH(Bn)NDipp}$]HfBn$_2$ | MAO | 80 | 37 | 5 | 473,420 | 236,206 | 2 |
| 21 | [L$^{FcCH2NDipp}$]ZrBn$_2$ | [PhNMe$_2$H]B(C$_6$F$_5$)$_4$ | 50 | 2 | n.d. | n.d. | n.d. | n.d. |
| 22 | [L$^{FcCH2NDipp}$]ZrBn$_2$ | [PhNMe$_2$H]B(C$_6$F$_5$)$_4$ | 80 | 5 | n.d. | n.d. | n.d. | n.d. |
| 23 | [L$^{FcCH2NDipp}$]ZrBn$_2$ | MAO | 50 | 22 | n.d. | n.d. | n.d. | n.d. |
| 24 | [L$^{FcCH2NDipp}$]ZrBn$_2$ | MAO | 80 | 33 | 3 | 375,703 | 210,967 | 1.8 |

*Total volume = 5 mL, toluene solvent, 80 nanomols catalyst, 1 equiv [PhNMe$_2$H]B(C$_6$F$_5$)$_4$, 500 equiv MAO, ethylene pressure = 200 psig = 1.38 MPa = 13.8 bar, 0.1 mL Al(Oct)$_3$ (for runs using [PhNMe$_2$H]B(C$_6$F$_5$)$_4$ activator), 0.1 mL 1-octene. Activity is given in g · mmol$^{-1}$ · h$^{-1}$ · bar$^{-1}$. Bn stands for benzyl, Ph stands for phenyl, Me stands for methyl, Dipp stands for diisopropylphenyl. Catalyst abbreviations are shown in Chart 2. Mw and Mn values were determined by GPC.

Example Oligomerization to Hexene

Certain chromium-containing complexes when activated with an alumoxane are active catalysts for the selective trimerization of ethylene to form predominantly 1-hexene. Reactions were performed in a 48-well parallel pressure reactor which is described in WO 00/09255; U.S. Pat. Nos. 6,306,658; 6,455,316; 6,489,168; and J. Am. Chem., Soc. 2003, 125, pg. 4306. Results are shown in Table 2 and specific reaction details are included in a footnote to the table. To the heated and closed reactor was injected the activator solution (MMAO-3A is a modified methyl alumoxane cocatalyst type 3A commercially available from Akzo Chemicals, Inc. under the trade name Modified Methylalumoxane type 3A, covered under U.S. Pat. No. 5,041,584). Then the reactor was pressurized with ethylene to 2.76 MPa (400 psig) and the catalyst was injected as a solution. Reaction times were between 0.5 and 30 minutes and quenching was achieved by the introduction of air at 3.10 MPa (450 psig) to the wells. The crude samples were analyzed by gas chromatography to determine the relative amounts of the liquid oligomers formed. The volatiles were then removed under reduced pressure and the vials were weighed to determine the amount of polymer formed.

TABLE 2

Primary catalyst screening data for selective ethylene oligomerization.*

| run | catalyst | activator | T (° C.) | Selectivity for 1-hexene (mol %) | 1-hexene formation TOF ($h^{-1}$) | PE formed (mg) |
|---|---|---|---|---|---|---|
| 1 | [$L^{FcCH2NHBu}$]CrCl$_2$(thf) | MMAO-3A | 80 | >80 | 9213 | 1.6 |
| 2 | [$L^{FcCH2NHBu}$]CrCl$_2$(thf) | MMAO-3A | 80 | >80 | 8542 | 1.9 |
| 3 | [$L^{FcCH2NHPh}$]CrCl$_2$(thf) | MMAO-3A | 80 | low | 246 | 4.1 |
| 4 | [$L^{FcCH2NHPh}$]CrCl$_2$(thf) | MMAO-3A | 80 | low | 219 | 3.9 |
| 5 | [$L^{FcCH2NMe2}$]CrCl$_2$(thf) | MMAO-3A | 80 | low | 85 | 1.4 |
| 6 | [$L^{FcCH2NMe2}$]CrCl$_2$(thf) | MMAO-3A | 80 | low | 116 | 1.5 |

*Total volume = 5 mL, heptane solvent, 40 nanomols catalyst, 600 equiv MMAO-3A, 2.76 MPa (400 psig). Turn over frequency TOF (number of mols of 1-hexene divided by the number of mols of catalyst divided per hour) are given for the formation of 1-hexene. thf is tetrahydrofuran, Bu is butyl, Ph is phenyl, and Me is methyl. Catalyst abbreviations are shown in Chart 2.

All documents described are fully incorporated herein by reference, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A compound represented by the formula:

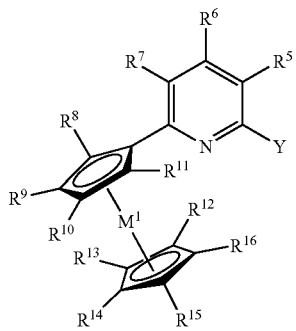

wherein $M^1$ is a metal atom selected from the group consisting of Fe, Ru, and Co;

Y is a reactive moiety selected from the group consisting of —CHO, —C(O)$R^4$ and or a halogen, and $R^4$ to $R^{16}$ are independently selected from the group consisting of hydrogen, alkyl, aryl, arylalkyl, halogen, alkoxy, aryloxy, amino, and silyl, and two adjacent carbon atoms of at least one cyclopentadienyl moiety may be linked by a saturated or unsaturated cyclic moiety having from 3 to 6 carbon atoms, optionally containing a heteroatom.

2. The compound or complex according to claim 1, in which $M^1$ is Fe or Ru and $R^8$ to $R^{16}$ are hydrogen.

3. The compound or complex according to claim 1, in which the alkyl, aryl, arylalkyl, silyl, aryloxy and alkoxy moieties comprise from 1 to 20 carbon atoms.

4. A compound for use as a ligand in a transition metal complex, the compound being represented by the formula:

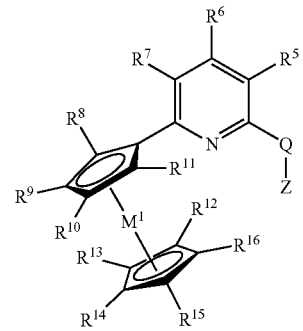

wherein $M^1$ is a metal atom selected from the group consisting of Fe, Ru, and Co;

Q is —$CR^3R^4$— or —$SiR^3R^4$—; and $R^1$ to $R^{16}$ are independently selected from the group consisting of hydrogen, alkyl, aryl, arylalkyl, halogen, alkoxy, aryloxy, amino, and silyl, Z is —$NR^1R^2$ ; and; two adjacent carbon atoms of at least one cyclopentadienyl moiety may be linked by a saturated or unsaturated cyclic moiety having from 3 to 6 carbon atoms, optionally containing a heteroatom, and $R^1$ and $R^2$ in —$NR^1R^2$ and $R^3$ and $R^4$ in $CR^3R^4$— or —$SiR^3R^4$ may form a chain of from 3 to 6 carbon atoms, optionally including a heteroatom.

5. The compound or complex according to claim 4, in which $M^1$ is Fe or Ru and $R^8$ to $R^{16}$ are hydrogen.

6. The compound or complex according to claim 4, in which the alkyl, aryl, arylalkyl, silyl, aryloxy and alkoxy moieties comprise from 1 to 20 carbon atoms.

7. A process for producing a metallocenyl pyridine compound which comprises reacting a metallocenylboronic acid with a pyridyl compound containing at least one pyridyl-halogen or triflate group in the presence of a Pd catalyst and producing a metallocenyl pyridine compound represented by the formula:

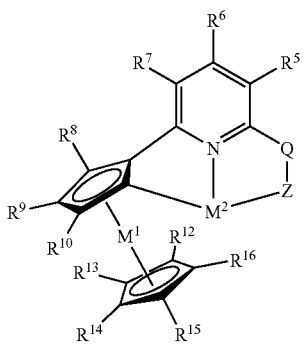

wherein $M^1$ is a metal atom selected from the group consisting of Fe, Ru, and Co;

Y is a reactive moiety selected from the group consisting of —CHO, —C(O)R$^4$ and or a halogen, and $R^4$ to $R^{16}$ are independently selected from the group consisting of hydrogen, alkyl, aryl, arylalkyl, halogen, alkoxy, aryloxy, amino, and silyl, and two adjacent carbon atoms of at least one cyclopentadienyl moiety may be linked by a saturated or unsaturated cyclic moiety having from 3 to 6 carbon atoms, optionally containing a heteroatom.

8. The process of claim 7, where the Pd catalyst comprises 1,1'-bis(diphenylphosphino)ferrocene.

9. A process according to claim 7, which comprises coupling a di-halo-pyridine or a halo-pyridine-aldehyde or halo-pyridine-ketyl species with a metallocenyl-based boronic acid to produce an intermediate compound in which —Y is halogen or —CHO or —C(O)R$^4$.

10. A process for producing a ligand precursor compound represented by formula (II) which comprises reacting a metallocenylboronic acid with a pyridyl compound containing at least one pyridyl-halogen or triflate group in the presence of a Pd catalyst and producing a metallocenyl pyridine compound represented by Formula (I):

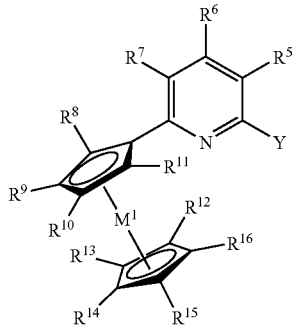

Formula (I)

wherein $M^1$ is a metal atom selected from the group consisting of Fe, Ru, and Co;

Y is a reactive moiety selected from the group consisting of —CHO, —C(O)R$^4$ and or a halogen, and $R^4$ to $R^{16}$ are independently selected from the group consisting of hydrogen, alkyl, aryl, arylalkyl, halogen, alkoxy, aryloxy, amino, and silyl, and two adjacent carbon atoms of at least one cyclopentadienyl moiety may be linked by a saturated or unsaturated cyclic moiety having from 3 to 6 carbon atoms, optionally containing a heteroatom, where the process comprises coupling a di-halo-pyridine or a halo-pyridine-aldehyde or halo-pyridine-ketyl species with a metallocenyl-based boronic acid to produce a compound in which —Y is halogen or —CHO or —C(O)R$^4$ as represented by Formula (I), thereafter lithiating the compound represented by Formula (I) in which —Y is halogen and reacting the lithio product with a mono- or dichloro silicon derivative and, optionally, an amine or metal amido reagent, or reacting the compound represented by Formula (I) in which —Y is —CHO or —C(O)R$^4$ with an amine and subsequently with an organometallic reagent to form a ligand precursor compound represented by the Formula (II):

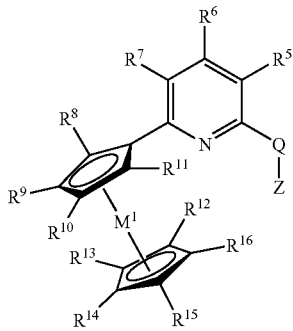

Formula (II)

wherein $M^l$, and $R^4$ to $R^{16}$ are as defined for Formula I;

Q is —CR$^3$R$^4$— or —SiR$^3$R$^4$—; Z is —NR$^1$R$^2$; and $R^l$ to $R^3$ are independently selected from the group consisting of hydrogen, alkyl, aryl, arylalkyl, halogen, alkoxy, aryloxy, amino, and silyl, and two adjacent carbon atoms of at least one cyclopentadienyl moiety may be linked by a saturated or unsaturated cyclic moiety having from 3 to 6 carbon atoms, optionally containing a heteroatom, and $R^l$ and $R^2$ in —NR$^1$R$^2$ and $R^3$ and $R^4$ in CR$^3$R$^4$— or —SiR$^3$R$^4$ may form a chain of from 3 to 6 carbon atoms, optionally including a heteroatom.

11. The process of claim 10, where the Pd catalyst comprises 1,1'-bis(diphenylphosphino)ferrocene.

12. A compound represented by the Formula (A) or Formula (B):
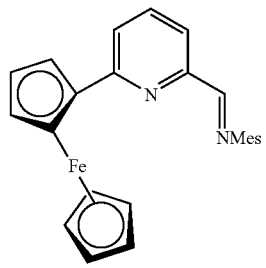
Formula (A)
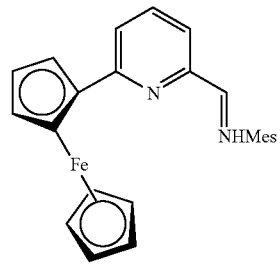
Formula (B)
where Mes is mesityl.
* * * * *